United States Patent
Sugahara

(10) Patent No.: US 12,226,251 B2
(45) Date of Patent: Feb. 18, 2025

(54) IMAGING SUPPORT DEVICE, AND OPERATION METHOD AND OPERATION PROGRAM FOR THE SAME

(71) Applicant: FUJIFILM CORPORATION, Tokyo (JP)

(72) Inventor: Masataka Sugahara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 228 days.

(21) Appl. No.: 17/744,771

(22) Filed: May 16, 2022

(65) Prior Publication Data

US 2022/0273256 A1 Sep. 1, 2022

Related U.S. Application Data

(63) Continuation of application No. PCT/JP2020/043699, filed on Nov. 24, 2020.

(30) Foreign Application Priority Data

Nov. 27, 2019 (JP) .................................. 2019-214743

(51) Int. Cl.
*A61B 6/00* (2024.01)
*A61B 6/46* (2024.01)
*G06T 7/33* (2017.01)

(52) U.S. Cl.
CPC .......... *A61B 6/5247* (2013.01); *A61B 6/4417* (2013.01); *A61B 6/463* (2013.01); *G06T 7/337* (2017.01)

(58) Field of Classification Search
CPC ......... A61B 6/022; A61B 6/08; A61B 6/4028; A61B 6/4233; A61B 6/4293;
(Continued)

(56) References Cited

U.S. PATENT DOCUMENTS

2015/0363926 A1 12/2015 Enomoto
2016/0206203 A1* 7/2016 Yu ........................... G06T 15/08
(Continued)

FOREIGN PATENT DOCUMENTS

CN 105073007 A 11/2015
CN 109953765 A 7/2019
(Continued)

OTHER PUBLICATIONS

English translation JP2014117368 (Year: 2014).*
(Continued)

*Primary Examiner* — Dani Fox
(74) *Attorney, Agent, or Firm* — SOLARIS Intellectual Property Group, PLLC

(57) ABSTRACT

An imaging support device used in a radiography apparatus including a radiation source and a radiation image detector that detects a radiation image of a subject on the basis of radiation emitted from the radiation source and transmitted through the subject, and includes an optical camera that optically images a region including an irradiation field of the radiation applied to the subject from the radiation source, and at least one processor. The processor acquires, as a first optical image, an optical image indicating the subject in the region by causing the optical camera to perform imaging in conjunction with radiography performed by the radiography apparatus, and stores a radiation image acquired through the radiography and the first optical image in a storage unit in association with each other.

10 Claims, 24 Drawing Sheets

(58) Field of Classification Search
CPC ....... A61B 6/4405; A61B 6/464; A61B 6/465; A61B 6/467; A61B 6/469; A61B 6/547; A61B 6/563; A61B 6/587; A61B 6/588
See application file for complete search history.

(56) References Cited

U.S. PATENT DOCUMENTS

| | | |
|---|---|---|
| 2017/0065370 A1 | 3/2017 | Nakai |
| 2018/0035968 A1 | 2/2018 | Yamahana |
| 2019/0046130 A1 | 2/2019 | Imamura et al. |
| 2019/0183448 A1 | 6/2019 | Horiuchi et al. |

FOREIGN PATENT DOCUMENTS

| | | |
|---|---|---|
| JP | 2011-024721 A | 2/2011 |
| JP | 2014-117368 A | 6/2014 |
| JP | 2016-150155 A | 8/2016 |
| JP | 2017-217227 A | 12/2017 |
| JP | 2017-217479 A | 12/2017 |
| JP | 2019-033830 A | 3/2019 |

OTHER PUBLICATIONS

Extended European Search Report dated Dec. 5, 2022, issued in corresponding EP Patent Application No. 20893265.7.
English language translation of the following: Office action dated Nov. 22, 2022 from the JPO in a Japanese patent application No. 2021-561432 corresponding to the instant patent application.
International Search Report issued in International Application No. PCT/JP2020/043699 on Feb. 2, 2021.
Written Opinion of the ISA issued in International Application No. PCT/JP2020/043699 on Feb. 2, 2021.
English language translation of the following: Office action dated Oct. 26, 2024 from the SIPO in a Chinese patent application No. 202080082472.X corresponding to the instant patent application. This office action translation is submitted now in order to supplement the understanding of the cited references which are being disclosed in the instant Information Disclosure Statement.

* cited by examiner

| IMAGING TECHNIQUE | IRRADIATION CONDITIONS |
|---|---|
| KNEE/BENDING POSTURE/SIDE | TUBE VOLTAGE: 50 kV<br>TUBE CURRENT: 150 mA<br>IRRADIATION TIME: 15 ms |
| CHEST/LYING POSTURE/FRONT | TUBE VOLTAGE: 100 kV<br>TUBE CURRENT: 200 mA<br>IRRADIATION TIME: 20 ms |
| CHEST/LYING POSTURE/BACK | TUBE VOLTAGE: 120 kV<br>TUBE CURRENT: 220 mA<br>IRRADIATION TIME: 25 ms |

38

FIG. 8
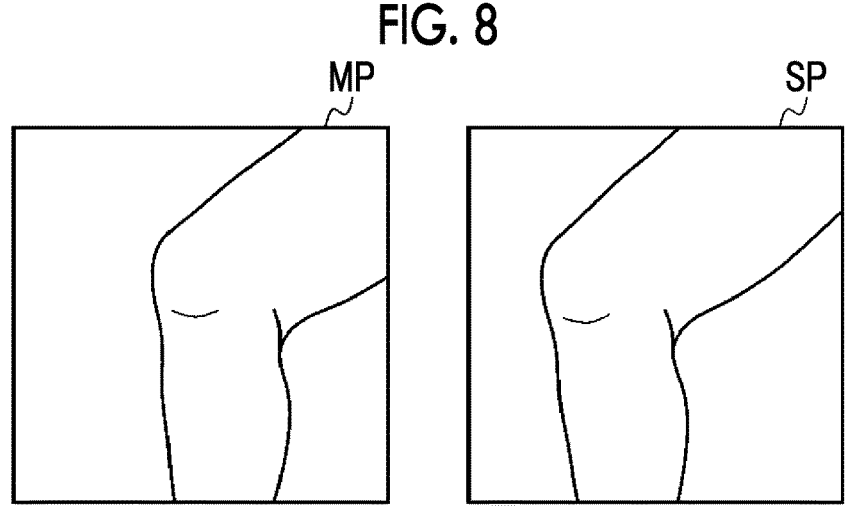
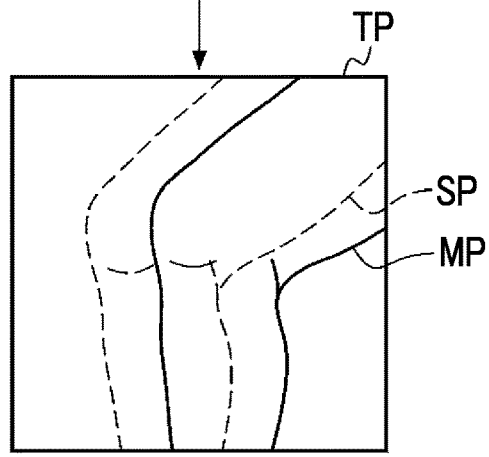
FIG. 9
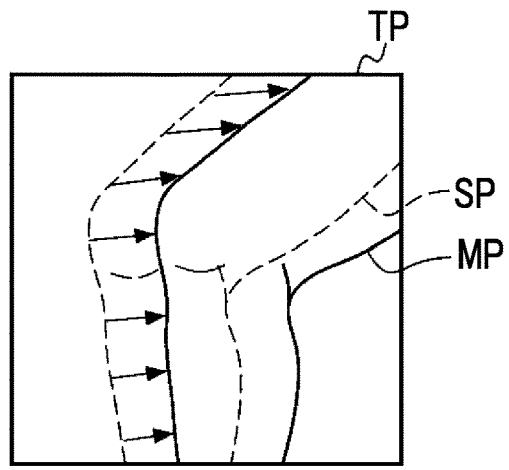

IMAGING SUPPORT DEVICE, AND OPERATION METHOD AND OPERATION PROGRAM FOR THE SAME

CROSS-REFERENCE TO RELATED APPLICATIONS

This application is a continuation application of International Application No. PCT/JP2020/043699, filed Nov. 24, 2020, the disclosure of which is incorporated herein by reference in its entirety. Further, this application claims priority from Japanese Patent Application No. 2019-214743, filed on Nov. 27, 2019, the disclosure of which is incorporated herein by reference in its entirety.

BACKGROUND

1. Technical Field

The technique of the present disclosure relates to an imaging support device, and an operation method and an operation program for the same.

2. Description of the Related Art

In a radiography system used in the medical field, a radiologist or a doctor (hereinafter referred to as a technician or the like) positions an imaging site of a subject in preparation for imaging, and then radiography is performed on the basis of instructions from the technician or the like. However, after positioning an imaging site with respect to an irradiation field of radiation and before radiography is performed, the subject may move to cause a misregistration of an imaging site, and an image of a desired imaging site may not be obtained. As described above, a failure to obtain a desired radiation image through radiography, that is, a failure in radiography is referred to as an "imaging failure". In a case where there is imaging failure, reimaging will be performed. The reimaging preferably takes less time and effort.

Therefore, for example, in a radiography system disclosed in JP2011-24721A, reimaging is suppressed by providing an optical camera that captures an optical image of a subject. In a case of performing radiography in the radiography system described in JP2011-24721A, first, in a case where a technician or the like positions an imaging site while guiding a subject, a positioning state of the imaging site at that time is imaged by the optical camera. Thereafter, immediately before the radiography, a positioning state of the imaging site is imaged again by the optical camera. By comparing a positioning image captured by the optical camera at the time of positioning the imaging site with a current image captured by the camera immediately before radiography, the technician or the like visually checks the presence or absence of a misregistration of the imaging site. Since radiography can be performed after such checking, unnecessary reimaging is suppressed.

SUMMARY

However, depending on an imaging site, even in a case where a technician or the like thinks that positioning is accurate, the positioning is not actually performed properly, and as a result, there is a slight misregistration that causes imaging failure. For example, in a case of diagnosing a state of a knee joint on the basis of a radiation image of the knee as an imaging site, a joint cavity (gap between bones) needs to be clearly depicted in the radiation image. However, since radiation is a flux of light that radially diverges from a focal point of a radiation source, an incident angle of the radiation may change due to a slight misregistration of the joint, and thus the depiction of the joint cavity may become unclear. In a case where the depiction of the joint cavity is unclear, imaging failure will occur and reimaging will be required.

In a case where reimaging is required due to imaging failure as described above, a technician or the like needs to position a subject again. In a case where a slight misregistration of the subject is adjusted in order to perform reimaging, it is often sufficient to perform fine adjustment with a position of the subject at the time of imaging failure as a reference. However, in a case where the subject moves significantly from the time of the imaging failure, the technician or the like cannot accurately ascertain the position of the subject at the time of imaging failure, and cannot perform fine adjustment. In a case where the subject is repositioned from the beginning without using the position at the time of imaging failure as a reference, a possibility of the occurrence of imaging failure again increases.

It is conceivable to adjust a position of a subject on the basis of a radiation image at the time of imaging failure when performing reimaging, but since the radiation image does not depict an appearance of the subject, it is not realistic to perform a position adjustment of the subject on the basis of the radiation image.

As described above, depending on an imaging site, reimaging may be unavoidable, but in a case where a position adjustment at the time of reimaging cannot be performed properly, even though reimaging is performed, imaging failure is likely to occur, and reimaging may be repeated.

A technique of the present disclosure provides an imaging support device, and an operation method and an operating program for the same capable of suppressing repetition of reimaging.

In order to achieve the above object, according to the present disclosure, there is provided an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source, and at least one processor. The processor acquires, as a first optical image, an optical image indicating the subject in the region by causing the optical camera to perform imaging in conjunction with radiography performed by the radiography apparatus, and stores a radiation image acquired through the radiography and the first optical image in a storage unit in association with each other.

It is preferable that the processor acquires, as a second optical image, an optical image indicating the subject in the region by causing the optical camera to perform imaging after the radiography is performed, and superimposes the first optical image on the second optical image to be displayed on a display.

It is preferable that the first optical image is a still image, and the second optical image is a motion picture, and the processor superimposes the second optical image on the first optical image, and displays the superposition result on the display in real time.

It is preferable that the processor detects a misregistration amount of the subject between the first optical image and the second optical image through image processing, and supplies information regarding the misregistration amount to a notification unit.

It is preferable that the notification unit is the display, and the processor displays, on the display, a direction in which a position of the subject is moved to a position indicated by the first optical image on the basis of the misregistration amount.

The processor may output a warning from the notification unit in a case where the misregistration amount is equal to or more than a certain value.

It is also preferable that the radiography apparatus further includes a movement mechanism that moves the irradiation field of the radiation, and the processor controls the movement mechanism such that the irradiation field is moved in a direction in which the misregistration amount decreases.

The optical camera preferably performs imaging on the basis of visible light or infrared rays.

The imaging support device preferably further includes a projector that projects the first optical image onto the radiation image detector.

According to the present disclosure, there is provided an operation method for an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source, the operation method including acquiring an optical image indicating the subject in the region by causing the optical camera to perform imaging in conjunction with radiography performed by the radiography apparatus; and storing a radiation image acquired through the radiography and the optical image in a storage unit in association with each other.

According to the present disclosure, there is provided an operation program for operating an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source and at least one processor, the operation program causing the processor to execute an operation of acquiring an optical image indicating the subject in the region by causing the optical camera to perform imaging in conjunction with radiography performed by the radiography apparatus; and an operation of storing a radiation image acquired through the radiography and the optical image in a storage unit in association with each other.

According to the technique of the present disclosure, it is possible to provide an imaging support device, and an operation method and an operation program for the same capable of suppressing repetition of reimaging.

BRIEF DESCRIPTION OF THE DRAWINGS

Exemplary embodiments according to the technique of the present disclosure will be described in detail based on the following figures, wherein:

FIG. 8 is a diagram exemplifying a superposition process, FIG. 9 is a diagram exemplifying misregistration detection.

DETAILED DESCRIPTION

First Embodiment

Figure 1:
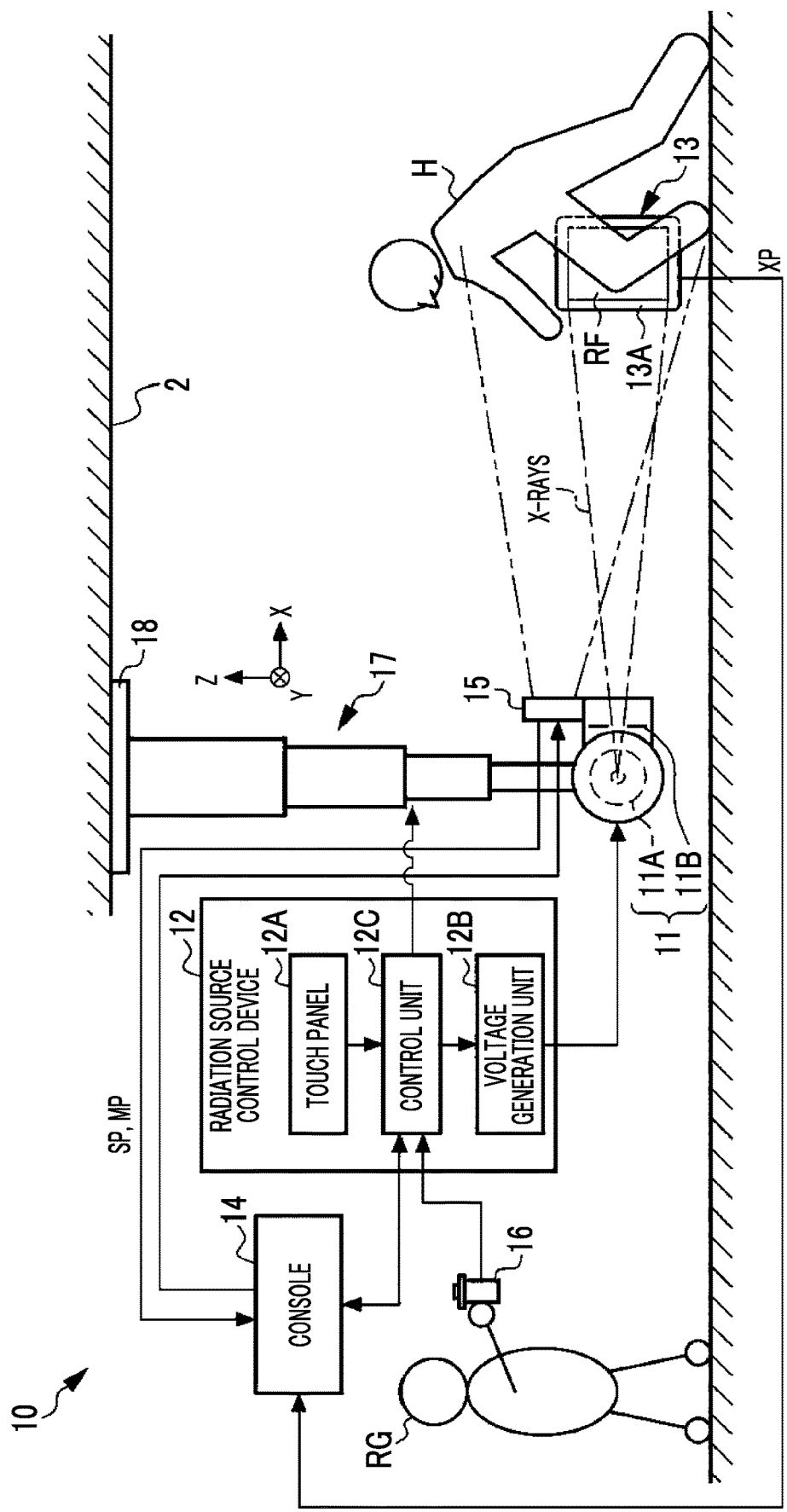
FIG. 1 is a diagram showing a configuration of an X-ray imaging system.

In FIG. 1, an X-ray imaging system 10 that uses X-rays as radiation includes an X-ray source 11, a radiation source control device 12, an electronic cassette 13, a console 14, and an optical camera 15. In the present embodiment, an imaging support device is configured by the console 14 and the optical camera 15. The X-ray source 11 is an example of a radiation source. The electronic cassette 13 is an example of a radiation image detector.

In the X-ray imaging system 10, the electronic cassette 13 is disposed at a position facing the X-ray source 11. By disposing a subject H between the X-ray source 11 and the electronic cassette 13, it is possible to capture an X-ray image of an imaging site (knee in FIG. 1) of the subject H. The X-ray source 11 and the electronic cassette 13 configure an X-ray imaging apparatus. This X-ray imaging apparatus is an example of a radiography apparatus.

The electronic cassette 13 may be disposed by using an imaging table. In the present embodiment, it is assumed that the radiologist (hereinafter, simply referred to as a technician) RG positions the subject H, and then the technician RG performs an X-ray imaging operation.

The X-ray source 11 includes an X-ray tube 11A that generates X-rays and an irradiation field limiter 11B that limits an irradiation field RF that is a region irradiated with X-rays. The X-ray source 11 may include an irradiation field display light source (not shown) that emits irradiation field display light indicating the irradiation field RF on an X-ray incident surface 13A of the electronic cassette 13.

The X-ray tube 11A has a filament that emits thermions and a target that collides with the thermions emitted from the filament and emits X-rays. In the irradiation field limiter 11B, for example, by disposing four lead plates that shield X-rays on respective quadrangular sides, a quadrangular irradiation opening for transmitting X-rays is formed at the center. In this case, the irradiation field limiter 11B changes a size of the irradiation opening by moving positions of the lead plates, and sets the irradiation field RF.

The radiation source control device 12 has a touch panel 12A, a voltage generation unit 12B, and a control unit 12C. The touch panel 12A is operated by the technician RG in a case where X-rays irradiation conditions and a size of the irradiation opening of the irradiation field limiter 11B are set. The X-ray irradiation conditions include a tube voltage and a tube current applied to the X-ray source 11, and the X-ray irradiation time.

The voltage generation unit 12B generates a tube voltage applied to the X-ray tube 11A. By controlling an operation of the voltage generating unit 12B, the control unit 12C sets the tube voltage, the tube current, and the X-ray irradiation time to values set by using the touch panel 12A. The control unit 12C has a timer that starts clocking in a case where X-rays are generated from the X-ray tube 11A. The control unit 12C stops the operation of the X-ray tube 11A, for example, when the time measured by the timer reaches the irradiation time defined in the irradiation conditions. The control unit 12C operates the irradiation field limiter 11B, and sets the size of the irradiation opening to a size set by using the touch panel 12A.

An irradiation switch 16 is connected to the control unit 12C via a cable or the like. The irradiation switch 16 is operated by the technician RG in a case where irradiation of X-rays is started. In a case where the irradiation switch 16 is operated, the radiation source control device 12 generates X-rays in the X-ray tube 11A. Consequently, X-rays are applied toward the irradiation field RF.

The electronic cassette 13 detects an X-ray image XP based on X-rays emitted from the X-ray source 11 and transmitted through the imaging site of the subject H. The electronic cassette 13 has a wireless communication unit and a battery, and performs an operation wirelessly. The electronic cassette 13 wirelessly transmits the detected X-ray image XP to the console 14. The X-ray image XP is an example of a radiation image.

The X-ray source 11 is suspended vertically downward from a ceiling 2 of an imaging room. The X-ray source 11 is held by a suspension holding mechanism 17. The suspension holding mechanism 17 is attached to the ceiling 2 via a horizontal movement mechanism 18. The suspension holding mechanism 17 holds the X-ray source 11 in a vertical direction ($\pm Z$ direction) to be able to be moved up and down. The horizontal movement mechanism 18 movably holds the suspension holding mechanism 17 in an X-ray irradiation axis direction ($\pm X$ direction) and a direction ($\pm Y$ direction) orthogonal to the X-ray irradiation axis direction of the X-ray source 11.

A motor (not shown) is provided in each of the suspension holding mechanism 17 and the horizontal movement mechanism 18, and it is possible to move the X-ray source 11 manually or electrically in each direction. Operations of the suspension holding mechanism 17 and the horizontal movement mechanism 18 are controlled by the control unit 12C. Whether to move the X-ray source 11 manually or electrically may be selected by using the touch panel 12A. By moving the X-ray source 11, a position of the irradiation field RF can be adjusted.

The optical camera 15 is an optical digital camera configured to include a complementary metal oxide semiconductor (CMOS) type image sensor or a charge coupled device (CCD) type image sensor, and performing imaging based on visible light as an example. The optical camera 15 enables still image imaging and motion picture imaging. An optical axis of the optical camera 15 is parallel to the irradiation axis of X-rays passing through the center of the irradiation field RF. The optical camera 15 images a region including the irradiation field RF and generates an optical image. The optical image is an image indicating the imaging site of the subject H located in the irradiation field RF. The optical image is, for example, a color still image or motion picture.

The optical camera 15 is attached to an outer peripheral portion of the X-ray source 11. The optical camera 15 does not have to be attached to the outer peripheral portion of the X-ray source 11, or may be built in the X-ray source 11. In the optical camera 15, an objective lens and an imaging element may be configured separately. In this case, the objective lens may be disposed on the outer peripheral portion of the X-ray source 11 and the imaging element may be built in a portion other than the X-ray source 11 (for example, an arm supporting the X-ray source 11).

The optical camera 15 is connected to the console 14 by wire or wirelessly. The console 14 functions as an imaging control device to control an imaging operation of the optical camera 15. The console 14 causes the optical camera 15 to capture a still image in conjunction with X-ray imaging, and also to capture a motion picture during an imaging preparation period before the start of the X-ray imaging. For example, the console 14 is installed in an operation room adjacent to the imaging room in which the X-ray source 11 is installed.

The console 14 transmits a still image capturing command signal to the optical camera 15 in a case where the irradiation switch 16 is operated. The optical camera 15 captures a still image of a region including the irradiation field RF in response to the still image capturing command signal input from the console 14. An optical image (hereinafter referred to as a still image SP) obtained through this still image capturing is transmitted to the console 14.

The console 14 transmits a motion picture capturing start signal to the optical camera 15 in a case where an operation of starting imaging preparation is performed by the technician RG. The optical camera 15 starts to capture a motion picture of a region including the irradiation field RF in response to the motion picture capturing start signal input from the console 14. An optical image (hereinafter referred to as a motion picture MP) obtained through this motion picture capturing is transmitted to the console 14 as a so-called live view image in real time at the time of motion picture capturing.

Figure 2:
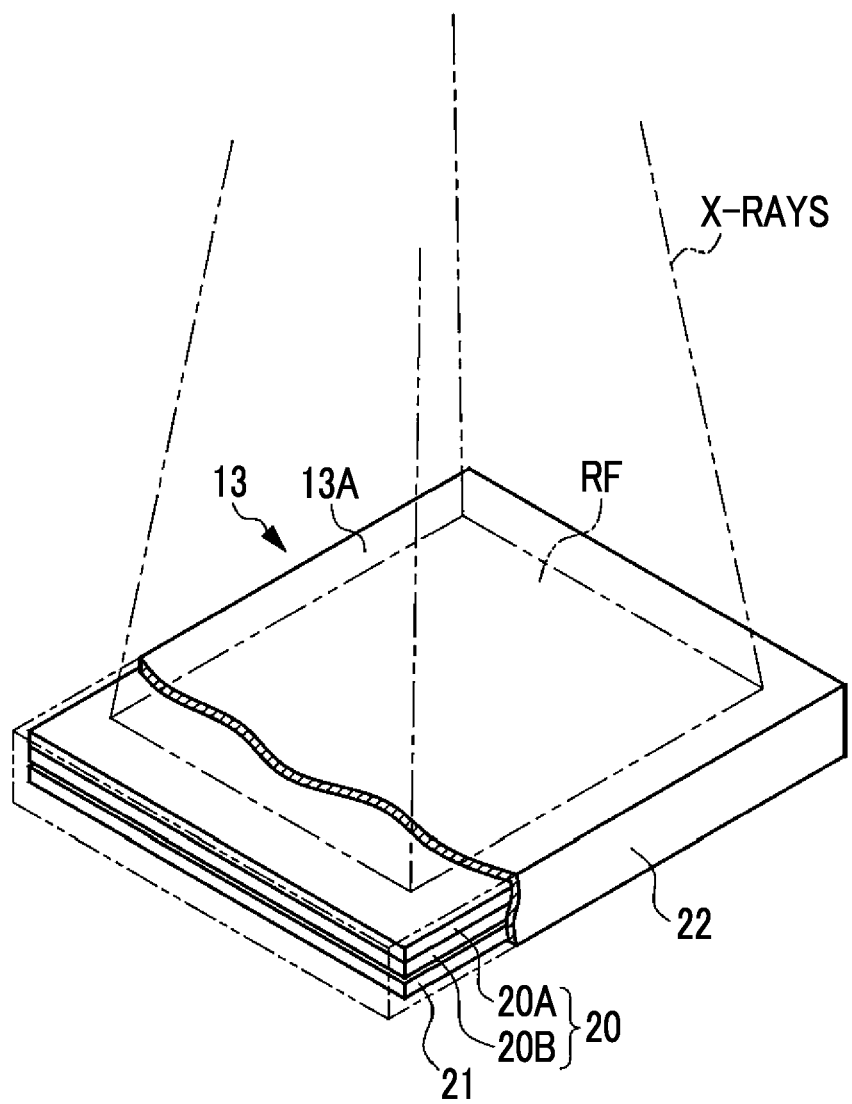
FIG. 2 is an external perspective view of an electronic cassette.

In FIG. 2, the electronic cassette 13 includes a sensor panel 20, a circuit unit 21, and a rectangular parallelepiped-shaped portable casing 22 that accommodates the sensor panel 20. The casing 22 has a size conforming to the international standard International Organization for Standardization (ISO) 4090:2001, which is substantially the same as that of, for example, a film cassette, an imaging plate (IP) cassette, or a computed radiography (CR) cassette.

The electronic cassette 13 is positioned in a posture in which the X-ray incident surface 13A that is an upper surface of the casing 22 faces the X-ray source 11, and the X-ray incident surface 13A is irradiated with X-rays. Although not shown, the casing 22 is also provided with a switch for switching between turning-on and turning-off of a main power source, and an indicator for reporting an operation state of the electronic cassette 13 such as a remaining battery usage time or an imaging ready state.

The sensor panel 20 is configured with a scintillator 20A and a light detection substrate 20B. The scintillator 20A and the light detection substrate 20B are laminated in the order of the scintillator 20A and the light detection substrate 20B when viewed from the X-ray incident surface 13A side. The scintillator 20A has phosphors such as CsI: Tl (thallium-activated cesium iodide) or GOS ($Gd_2O_2S$: Tb, terbium-activated gadolinium oxysulfide), and converts X-rays incident via the X-ray incident surface 13A into visible light and emits the visible light. A sensor panel in which the light detection substrate 20B and the scintillator 20A are laminated in this order when viewed from the X-ray incident surface 13A side may be used. A direct conversion type sensor panel that directly converts X-rays into signal charge with a photoconductor such as amorphous selenium may be used.

The light detection substrate 20B detects the visible light emitted from the scintillator 20A and converts the visible light into electric charge. The circuit unit 21 controls the drive of the light detection substrate 20B and generates the X-ray image XP on the basis of the electric charge output from the light detection substrate 20B.

A plurality of pixels are arranged in a two-dimensional matrix on the light detection substrate 20B. Each pixel photoelectrically converts the visible light emitted by the scintillator 20A to generate and store electric charge. The X-ray image XP is generated by converting the electric charge stored in each pixel into a digital signal in the circuit unit 21.

The electronic cassette 13 has a function of detecting, for example, the start of X-ray irradiation. This irradiation start detection function is realized by, for example, an irradiation start detection sensor provided on the light detection substrate 20B. The irradiation start detection sensor is configured with, for example, some of a plurality of pixels disposed in a two-dimensional matrix. In a case where a dose signal periodically output from the irradiation start detection sensor exceeds a threshold value, it is determined that the X-ray irradiation has started.

The electronic cassette 13 has a timer that starts clocking when the start of X-ray irradiation is detected, in the same manner as the radiation source control device 12. The electronic cassette 13 determines that the X-ray irradiation is finished when the time measured by the timer reaches the irradiation time included in the irradiation conditions set for the console 14. Thereby, the electronic cassette 13 can detect the X-ray image XP based on the applied X-ray by performing the X-ray detection operation only for a period corresponding to the irradiation time included in the irradiation conditions.

The electronic cassette 13 has an image memory and a wireless communication circuit. The electronic cassette 13 stores the X-ray image XP generated by the circuit unit 21 in the image memory, and transmits the X-ray image XP stored in the image memory to the console 14 with the wireless communication circuit.

Figure 3:
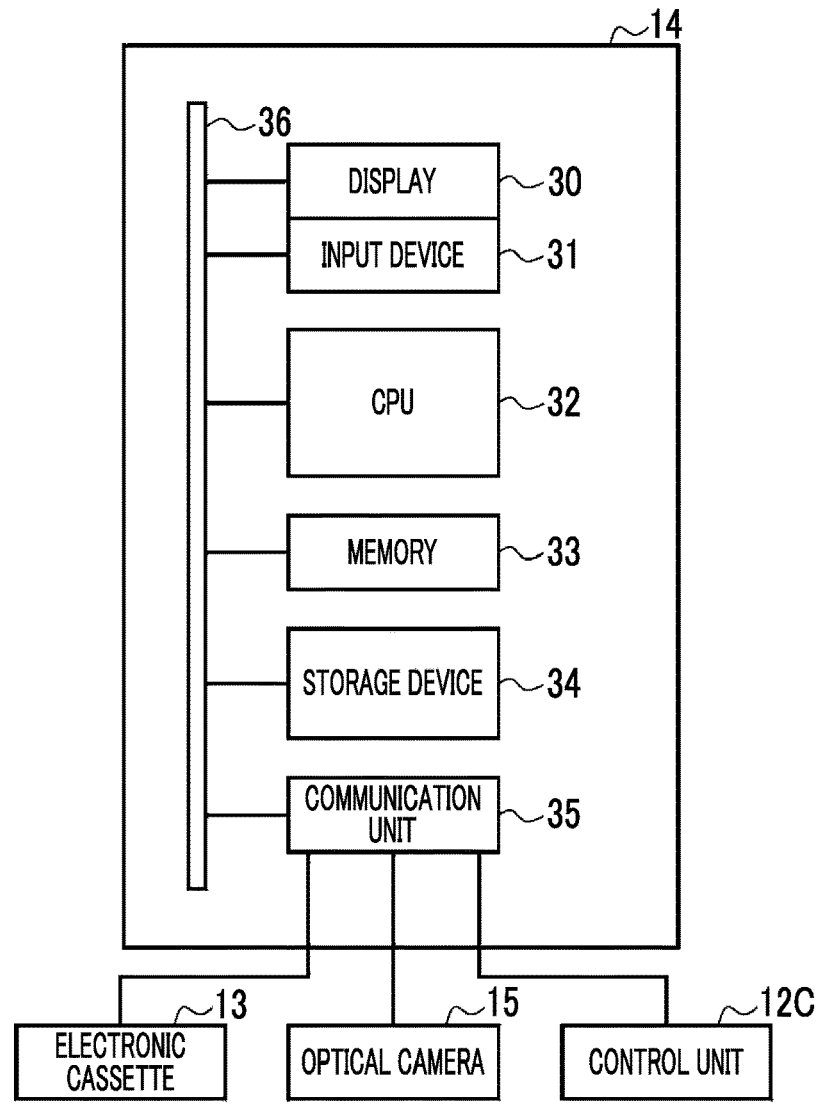
FIG. 3 is a block diagram showing a configuration of a console.

In FIG. 3, the console 14 includes a display 30, an input device 31, a central processing unit (CPU) 32, a storage device 34, a memory 33, and a communication unit 35. These constituents are connected to each other via a data bus 36.

The display 30 displays various operation screens provided with operation functions by a graphical user interface (GUI), the X-ray image XP, and the optical images (the still image SP and the motion picture MP). The input device 31 is an input operation unit including a touch panel, a keyboard, and the like.

The storage device 34 is, for example, a hard disk drive (HDD) array, which is built in the console 14 or externally connected to the console 14. External connection is made via a cables or a network. The storage device 34 stores control programs such as an operating system, various application programs, and various types of data associated with these programs.

The memory 33 is a work memory for the CPU 32 to execute a process. The CPU 32 collectively controls each unit of the console 14 by loading the program stored in the storage device 34 to the memory 33 and executing processes according to the program. The communication unit 35 transmits and receives various types of data such as the X-ray image XP and the optical images (the still image SP and the motion picture MP) to and from the electronic cassette 13 and the optical camera 15. The communication unit 35 communicates with the control unit 12C of the radiation source control device 12.

Figure 4:
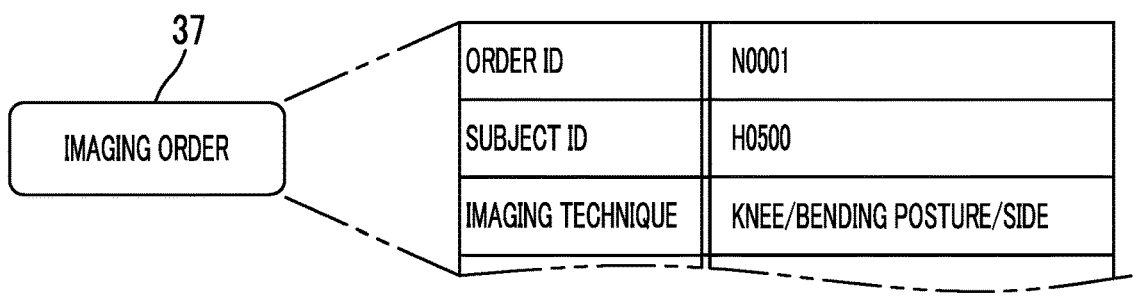
FIG. 4 is a diagram exemplifying an imaging order.

The console 14 receives input of an imaging order 37 shown in FIG. 4. The imaging order 37 is information for instructing the technician RG to perform X-ray imaging, for example, from an imaging requester in a clinical department. The imaging order 37 is delivered to the console 14 from, for example, a radiology information system (RIS) (not shown).

The imaging order 37 has items such as an order identification data (ID), a subject ID, and an imaging technique. The order ID is a symbol or number that identifies each imaging order 37, and is automatically assigned by the RIS. In the item of subject ID, a subject ID of the subject H who is an imaging target is written. The subject ID is a symbol or a number that identifies each subject H.

The imaging technique is information regarding an imaging site of the subject H and a posture and an orientation of the imaging site. In addition to the knees exemplified in FIG. 1, the imaging site includes the head, the cervical spine, the chest, the abdomen, hands, fingers, elbows, and the like. The posture is a posture of the subject H such as a standing posture, a lying posture, or a sitting posture. The orientation is an orientation of the subject H with respect to the X-ray source 11, such as the front, the side, or the back. In addition to these items, the imaging order 37 includes items of subject information such as the name, gender, age, height, and weight of the subject H.

Figures 5, 6:
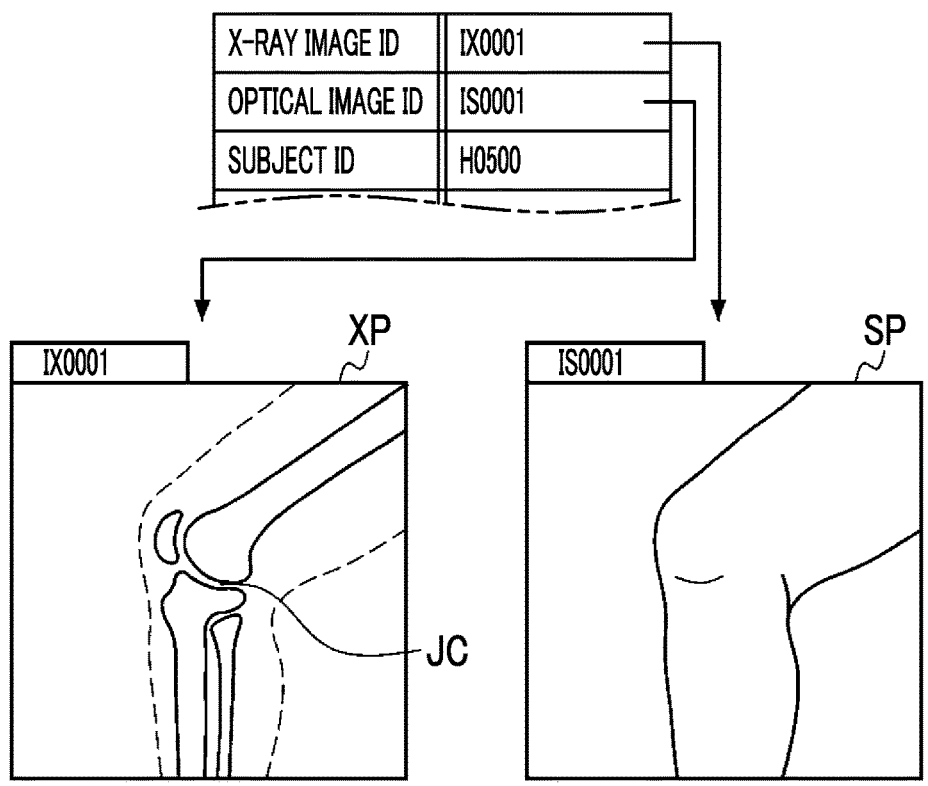
FIG. 5 is a diagram exemplifying a condition table.
FIG. 6 is a diagram exemplifying an X-ray image and still image that are associated with each other.

A condition table 38 shown in FIG. 5 is stored in the storage device 34 of the console 14. Irradiation conditions corresponding to each imaging technique are associated and registered in the condition table 38.

The console 14 displays an imaging order list that lists the details of the imaging order 37 shown in FIG. 4 on the display 30 through an operation of the technician RG. The technician RG may view the imaging order list and check the details of the imaging order 37. The console 14 displays the details of the condition table 38 shown in FIG. 5 on the display 30. The technician RG may select and set irradiation conditions that match the imaging technique designated in the imaging order 37.

The console 14 wirelessly transmits condition setting signals including various types of information such as irradiation conditions set by the technician RG, an order ID, and a console ID as console identification information to the electronic cassette 13.

The console 14 stores the X-ray image XP received from the electronic cassette 13 in the storage device 34 that is a storage unit, for example, as an image file in a format conforming to the Digital Imaging and Communication in Medicine (DICOM) standard. In the image file, the X-ray image XP and accessory information are associated with each other by one image ID. The accessory information includes an order ID, a subject ID, an imaging technique, irradiation conditions, and the like.

The still image SP obtained by the optical camera 15 capturing a still image in conjunction with the X-ray imaging is added with an image ID (optical image ID) associated with an image ID (X-ray image ID) of the X-ray image XP obtained through the X-ray imaging. As shown in FIG. 6, the X-ray image XP and the still image SP obtained when X-ray imaging is performed once are stored in the storage device 34 in association with the X-ray image ID and the optical image ID.

In a case where the imaging technique is "knee/bending posture/side", a doctor makes a diagnosis of the joint cavity JC of the knee on the basis of the X-ray image XP. Therefore, it is necessary that the joint cavity JC is clearly depicted in the X-ray image XP.

Figure 7:
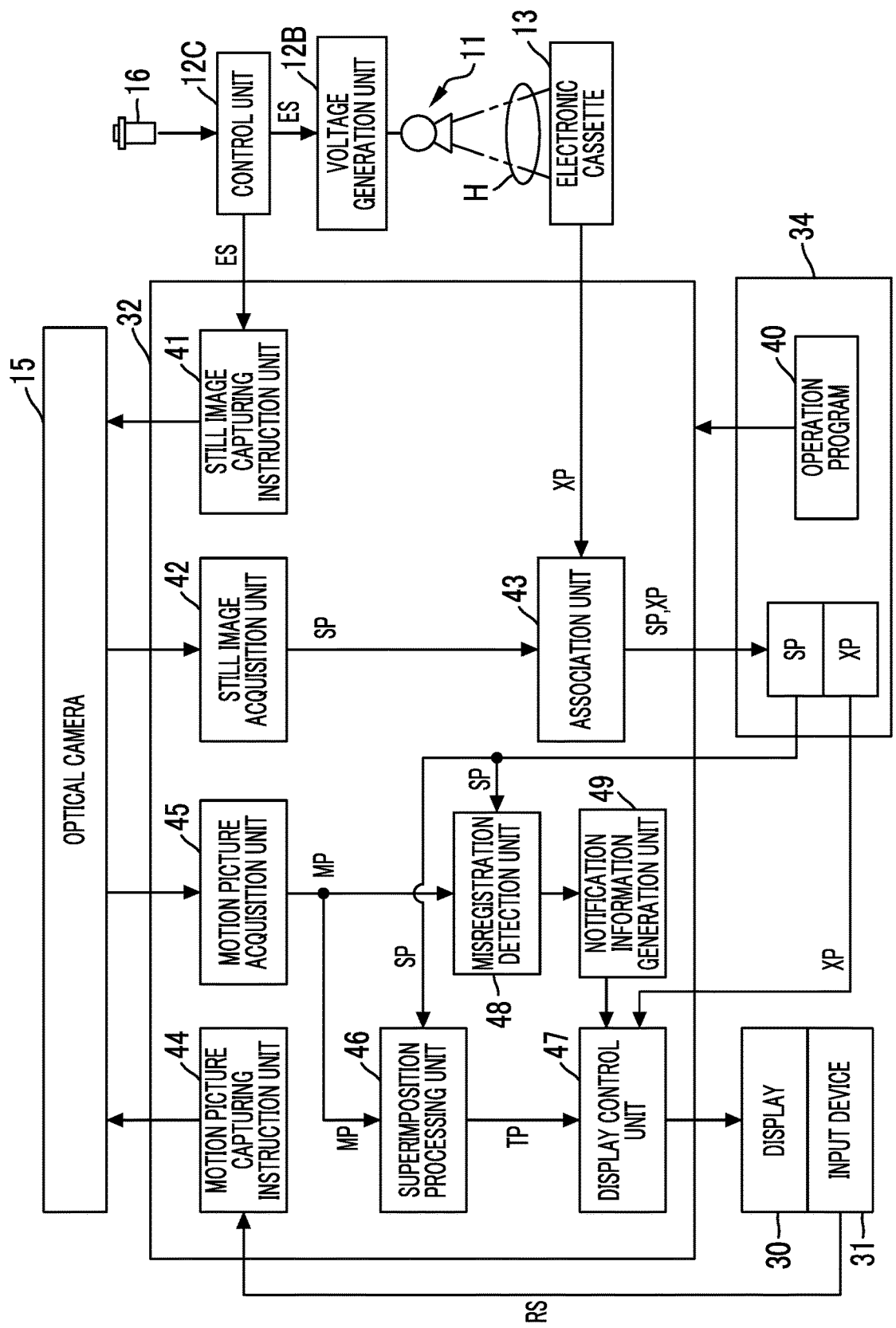
FIG. 7 is a block diagram showing each functional unit configured in a CPU.

In FIG. 7, the storage device 34 stores an operation program 40. Although not shown, the condition table 38 shown in FIG. 5 is also stored in the storage device 34. A plurality of functional units are configured in the CPU 32 by executing the operation program 40.

The operation program 40 uses the CPU 32 as a still image capturing instruction unit 41, a still image acquisition unit 42, an association unit 43, a motion picture capturing instruction unit 44, a motion picture acquisition unit 45, a superimposition processing unit 46, a display control unit 47, and a misregistration detection unit 48, and a notification information generation unit 49.

The still image capturing instruction unit 41 receives an X-ray irradiation start signal ES generated by the control unit 12C of the radiation source control device 12 and supplied to the voltage generation unit 12B in response to pressing of the irradiation switch 16. Upon receiving the X-ray irradiation start signal ES, the still image capturing instruction unit 41 instructs the optical camera 15 to execute still image capturing.

The still image acquisition unit 42 acquires the still image SP generated by the optical camera 15 capturing a still image. The still image SP acquired by the still image acquisition unit 42 is input to the association unit 43. The association unit 43 receives the X-ray image XP detected by the electronic cassette 13 on the basis of the X-rays emitted from the X-ray source 11 via the communication unit 35 in response to pressing of the irradiation switch 16.

The association unit 43 stores the still image SP input to the still image acquisition unit 42 and the X-ray image XP input from the electronic cassette 13 in the storage device 34 as shown in FIG. 6 in association with each other.

The motion picture capturing instruction unit 44 transmits a motion picture capturing start signal for instructing the optical camera 15 to start motion picture capturing in response to input of a reimaging preparation start signal RS from the input device 31. The technician RG checks the X-ray image XP acquired through X-ray imaging, and in a case where it is determined that there is imaging failure, the technician RG operates the input device 31 to cause the imaging support device to transition to a reimaging preparation mode. In a case where the imaging technique is "knee/bending posture/side", the technician RG determines that there is imaging failure in a case where, for example, the joint cavity JC of the knee is not clearly depicted in the X-ray image XP.

The motion picture acquisition unit 45 acquires, in real time for each frame, the motion picture MP generated by the optical camera 15 capturing a motion picture. The motion picture MP acquired by the motion picture acquisition unit 45 is input to the superimposition processing unit 46 for each frame.

The superimposition processing unit 46 acquires the still image SP stored in the storage device 34, and superimposes the still image SP on each frame of the motion picture MP as shown in FIG. 8. The superimposition processing unit 46 inputs a superimposition image TP generated by superimposing the motion picture MP and the still image SP to the display control unit 47 for each frame. The display control unit 47 displays the superimposition image TP on the display 30 for each frame. That is, the display control unit 47 superimposes the still image SP on the motion picture MP and displays it on the display 30 in real time.

The still image SP in the superimposition image TP is associated with the X-ray image XP in which the technician RG has determined that there is imaging failure, and is an example of a first optical image indicating a position of the subject H at the time of imaging failure. The motion picture MP in the superimposition image TP is an example of a second optical image indicating the current position of the subject H during reimaging preparation. Therefore, the technician RG can check the current position of the subject H with respect to the time of imaging failure by checking the superimposition image TP displayed in real time on the display 30.

The motion picture capturing of the optical camera 15 is finished in response to receiving an execution instruction for still image capturing from the still image capturing instruction unit 41 described above. The still image acquisition unit 42 may acquire one frame of the motion picture MP as the still image SP.

In the same manner as the superimposition processing unit 46, the misregistration detection unit 48 operates during a period in which the optical camera 15 is performing motion picture capturing. The motion picture MP acquired by the motion picture acquisition unit 45 is input to the misregistration detection unit 48 for each frame. The misregistration detection unit 48 acquires the still image SP stored in the storage device 34, and as shown in FIG. 9, performs image processing to detect a misregistration amount of the subject H between each frame of the motion picture MP and the still image SP. The misregistration detection unit 48 detects a misregistration amount by obtaining a movement vector by using, for example, a block matching method.

The misregistration detection unit 48 may detect a misregistration amount according to a machine learning method using a neural network. For example, the misregistration detection unit 48 may detect a misregistration amount by extracting feature amounts of the motion picture MP and the still image SP by using a convolutional neural network. According to the neural network, by learning various images of the subject H as training data, it is possible to accurately detect a misregistration due to rotation, turning, and the like without limitation to a case where the subject H moves in parallel.

Figure 10:
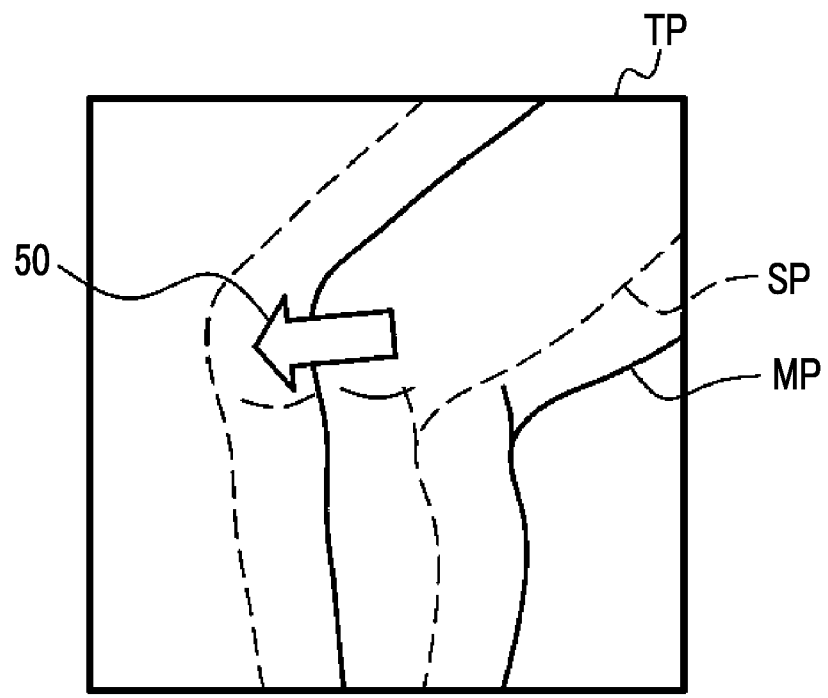
FIG. 10 is a diagram exemplifying a superimposition image.

The notification information generation unit 49 generates, as notification information, a direction (vector) in which the current position of the subject H indicated by the motion picture MP is moved to the position of the subject H at the time of imaging failure indicated by the still image SP, on the basis of the misregistration amount detected by the misregistration detection unit 48. This notification information is input to the display control unit 47. The display control unit 47 generates an arrow 50 indicating a direction included in the notification information, and displays the arrow 50 on the display 30 in a state in which the arrow is combined on the superimposition image TP as shown in FIG. 10, for example.

Since the misregistration detection unit 48 and the notification information generation unit 49 perform processing each time a frame of the motion picture MP is input, a direction and a size of the arrow 50 displayed on the display 30 are changed depending on movement of the subject H. For example, a size of the arrow 50 becomes smaller as a misregistration amount detected by the misregistration detection unit 48 is reduced. The technician RG can position the subject H to the position at the time of imaging failure indicated by the still image SP by giving an instruction to the subject H with voice or the like and guiding a position of the subject H in a direction in which the arrow 50 becomes smaller on the basis of the arrow 50 or the like displayed on the display 30. Therefore, the technician RG can position the subject H to the position at the time of imaging failure and finely adjust the position of the subject H with this position as a reference even in a case where the subject H moves significantly from the time of the imaging failure. In order for the technician RG to give an instruction to the subject H, a microphone may be provided in the operation room and a speaker may be provided in the imaging room. As described above, the technician RG can easily give an instruction for positioning to the subject H in the imaging room from the operation room.

Figure 11:
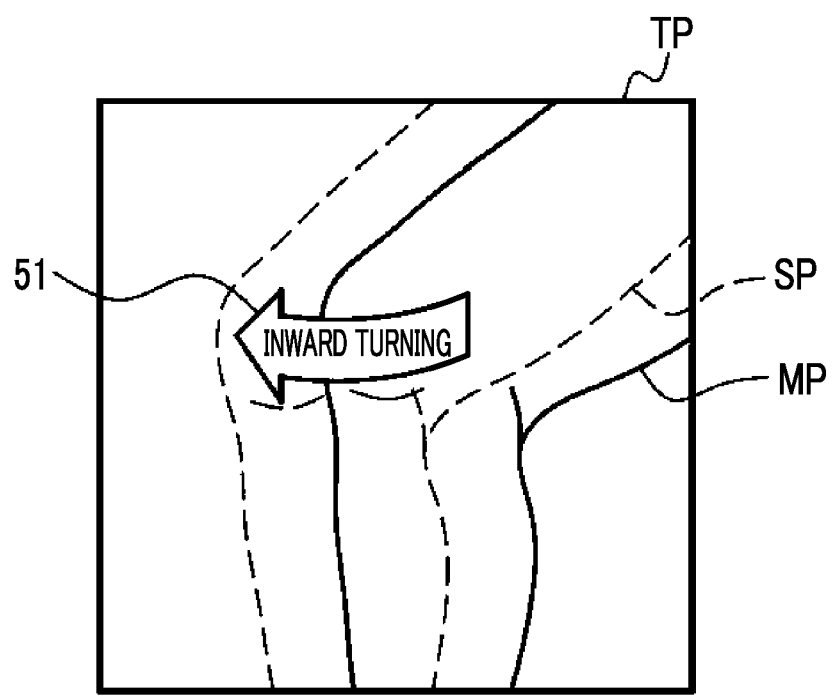
FIG. 11 is a diagram showing a modification example of an arrow displayed on a superimposition image.

In a case where the misregistration detection unit 48 can detect the misregistration due to rotation or turning, the notification information generation unit 49 may generate notification information indicating a direction of the rotation or the turning. FIG. 11 shows an example in which an arrow 51 indicating that the knee of the subject H should be turned inward in order to move the position of the subject H to the position at the time of imaging failure is displayed on the superimposition image TP. In this case, the internal turning is an operation in which the subject H turns the knee inward.

Next, an operation of the imaging support device having the above configuration will be described with reference to a flowchart of FIG. 12 and FIGS. 13 to 17. First, prior to imaging, the technician RG checks details of the imaging order 37 on the display 30, and sets irradiation conditions by using the input device 31 and the touch panel 12A. Next, the technician RG positions the X-ray source 11, the electronic cassette 13, and the subject H according to an imaging technique included in the imaging order 37. Here, the imaging technique is "knee/bending posture/side". The technician RG bends one leg of the subject H and positions the subject H such that the side of the knee faces the X-ray incident surface 13A of the electronic cassette 13 and the knee is located at the center of the irradiation field RF (refer to FIG. 1).

The still image capturing instruction unit 41 determines whether or not the X-ray irradiation start signal ES has been received from the control unit 12C of the radiation source control device 12 (step S10). The X-ray irradiation start signal ES is generated by the control unit 12C of the radiation source control device 12 in response to the technician RG pressing the irradiation switch 16 after positioning the subject H. The X-ray irradiation start signal ES generated by the control unit 12C is supplied to the voltage generation unit 12B and the console 14. The voltage generation unit 12B irradiates the subject H with X-rays from the X-ray source 11 in response to the X-ray irradiation start signal ES. The electronic cassette 13 detects the X-ray image XP of the subject H on the basis of the X-rays transmitted through the subject H.

In a case where the X-ray irradiation start signal ES has been received (step S10: YES), the still image capturing instruction unit 41 instructs the optical camera 15 to execute still image capturing (step S11). The still image acquisition unit 42 acquires the still image SP generated by the optical camera 15 capturing a still image (step S12). The console 14 acquires the X-ray image XP detected by the electronic cassette 13 (step S13).

Figure 13:
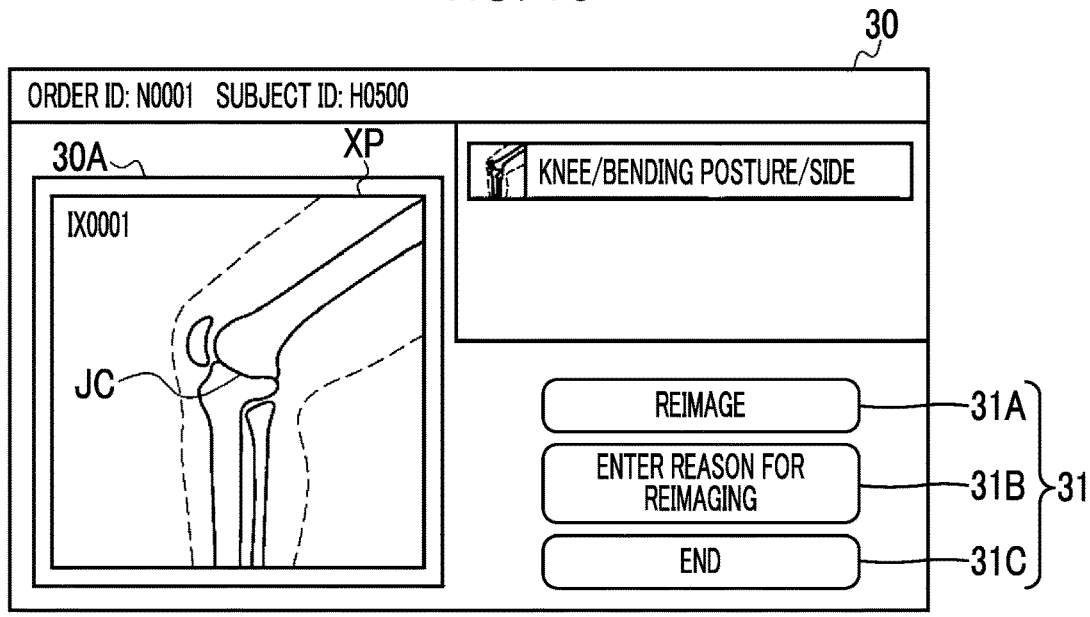
FIG. 13 is a diagram exemplifying an example of a screen of a display on which an X-ray image is displayed.

Next, the association unit 43 stores the acquired X-ray image XP and the still image SP in the storage device 34 in association with each other (step S14). The display control unit 47 displays the X-ray image XP stored in the storage device 34 on the display 30 (step S15). FIG. 13 shows an example of a screen of the display 30 on which the X-ray image XP is displayed. As shown in FIG. 13, the X-ray image XP is displayed on the display 30 in a image display region 30A.

The display 30 displays a first operation button 31A for performing reimaging, a second operation button 31B for inputting a reason for imaging failure, a third operation button 31C for performing an end operation, and the like. The first operation button 31A, the second operation button 31B, and the third operation button 31C configure an input device 31 and are operated by a touch panel formed on the screen of the display 30.

In a case where the technician RG checks the X-ray image XP displayed in the image display region 30A and determines that the image is favorable, the technician RG finishes the process related to the X-ray imaging by pressing the third operation button 31C.

Figure 14:
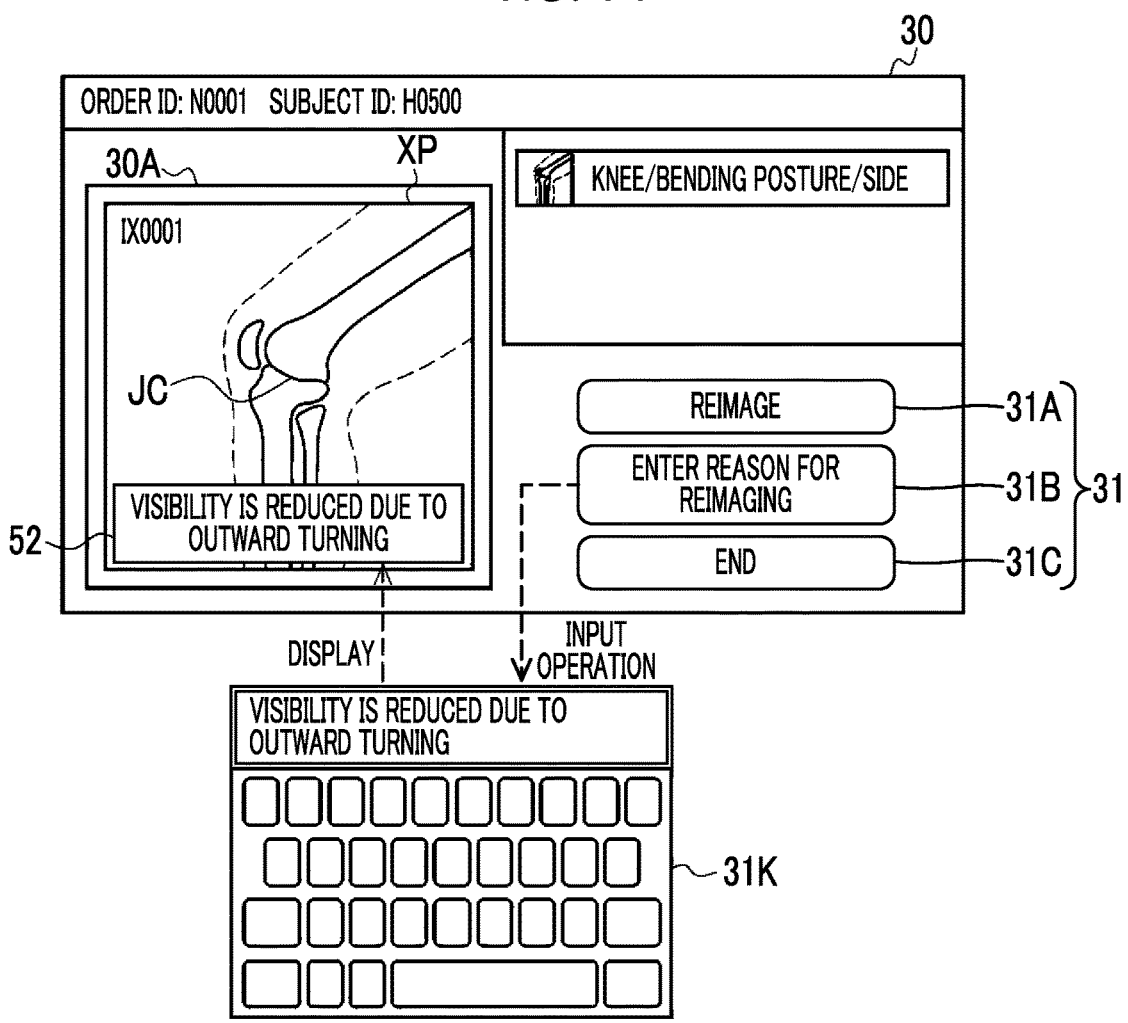
FIG. 14 is a diagram exemplifying a method of inputting a reason for imaging failure.

On the other hand, in a case where the X-ray image XP displayed in the image display region 30A is checked and it is determined that there is imaging failure, the technician RG can enter a reason for the imaging failure by using a keyboard 31K shown in FIG. 14 by pressing the second operation button 31B. An input reason for imaging failure 52 is displayed in the image display region 30A by the display control unit 47. The keyboard 31K is, for example, a virtual keyboard, and is operably displayed on the screen of the display 30 by the touch panel. The X-ray image XP shown in FIGS. 13 and 14 is an example in which the bones of the joint overlap with each other on the X-ray optical path due to outward turning of the knee, and thus the visibility of the joint cavity JC is reduced.

Figure 15:
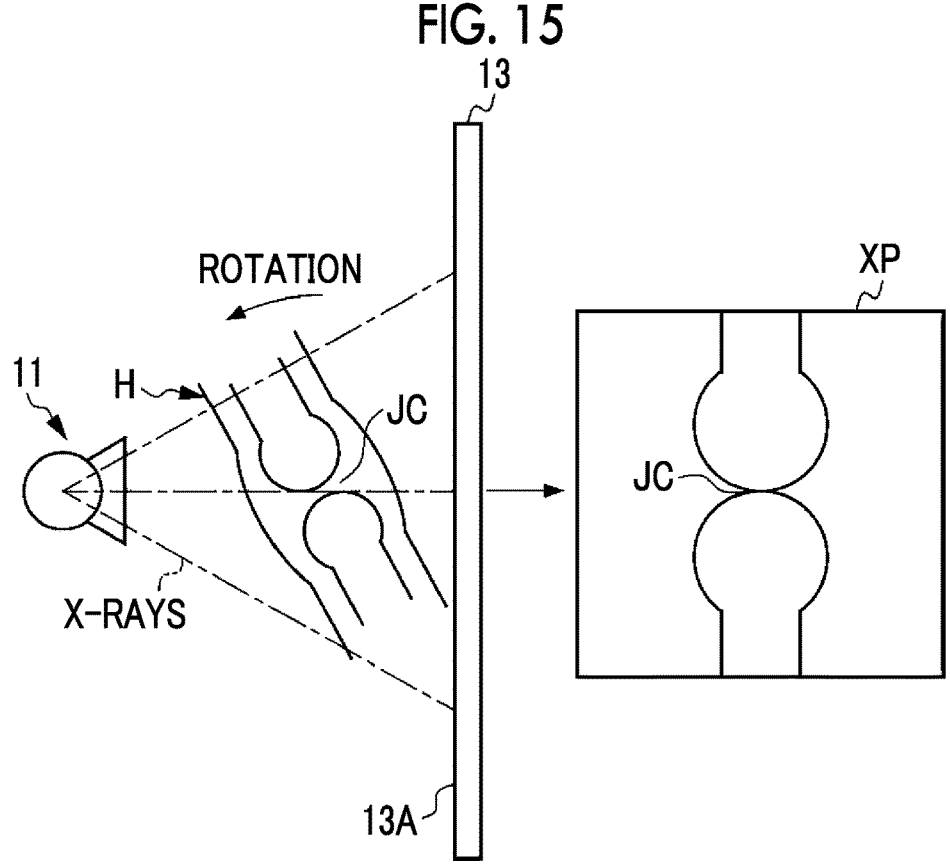
FIG. 15 is a diagram schematically showing a state in which the visibility of a joint cavity is reduced due to rotation of the knee.
Figure 16:
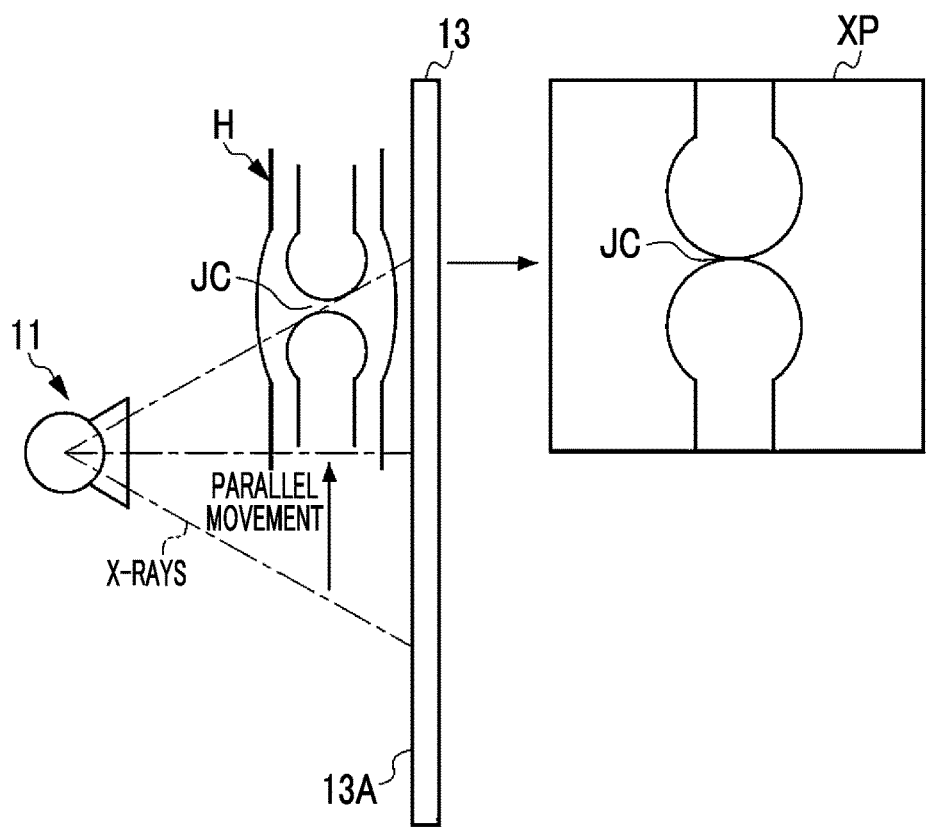
FIG. 16 is a diagram schematically showing how the legibility of the joint cavity is reduced due to the translation of a knee.

FIG. 15 schematically shows a state in which the visibility of the joint cavity JC is reduced in the X-ray image XP due to rotation of the knee. FIG. 16 schematically shows a state in which the visibility of the joint cavity JC is reduced in the X-ray image XP due to parallel movement of the knee. Since the X-rays applied to the subject H are a flux of light that radially diverges from a focal point of the X-ray source 11, a misregistration occurs in the subject H due to turning, rotation, or parallel movement, and thus an incidence angle of the X-rays with respect to the subject H changes such that the visibility of the joint cavity JC decreases. In reality, the joint cavity JC is narrow, and the knee misregistration occurs due to a combination of turning, rotation, parallel movement, and the like. Therefore, even a slight misregistration reduces the visibility of the joint cavity JC.

The technician RG presses the first operation button 31A in a case of performing reimaging (refer to FIG. 13). In a case where the first operation button 31A is pressed, the input device 31 generates the reimaging preparation start signal RS and transmits the signal to the motion picture capturing instruction unit 44.

Referring to FIG. 12 again, after step S15, it is determined whether or not the end operation has been performed by the technician RG pressing the third operation button 31C (step S16). In a case where it is determined that the end operation has been performed (step S16: YES), the process ends.

On the other hand, in a case where the end operation has not been performed (step S16: NO), it is determined whether or not the motion picture capturing instruction unit 44 has received the reimaging preparation start signal RS from the input device 31 (step S17). In a case where it is determined that the reimaging preparation start signal RS has been received (step S17: YES), the motion picture capturing instruction unit 44 transmits a motion picture capturing start signal to the optical camera 15 (step S18). The motion picture acquisition unit 45 acquires the motion picture MP generated by the optical camera 15 capturing a motion picture for each frame (step S19).

The superimposition processing unit 46 acquires the still image SP stored in the storage device 34, performs a process of superimposing the still image SP on the frame of the motion picture MP acquired by the motion picture acquisition unit 45, and generates the superposition image TP (step S20). The misregistration detection unit 48 acquires the still image SP stored in the storage device 34, and detects a misregistration amount of the subject H between the frame of the motion picture MP acquired by the motion picture acquisition unit 45 and the still image SP (step S21). The notification information generation unit 49 generates notification information indicating a direction (vector) in which the current position of the subject H is moved to the position of the subject H at the time of imaging failure, on the basis of the misregistration amount detected by the position deviation detection unit 48 (step S22).

The display control unit 47 generates an arrow (for example, the arrow 50 shown in FIG. 10) indicating the direction included in the notification information, and displays the arrow on the display 30 in a state in which the arrow is combined on the superimposition image TP (step S23). Thereafter, in the same manner as in step S10, it is determined whether or not the still image capturing instruction unit 41 has received the X-ray irradiation start signal ES from the control unit 12C (step S24).

While the still image capturing instruction unit 41 does not receive the X-ray irradiation start signal ES (step S24: NO), the process returns to step S19, and the motion picture acquisition unit 45 acquires the next frame of the motion picture MP. Until the X-ray irradiation start signal ES is received, the processes in steps S19 to S24 are repeatedly executed. Consequently, the superimposition image TP in which the still image SP is superimposed on the motion picture MP is displayed on the display 30 in real time.

Figure 17:
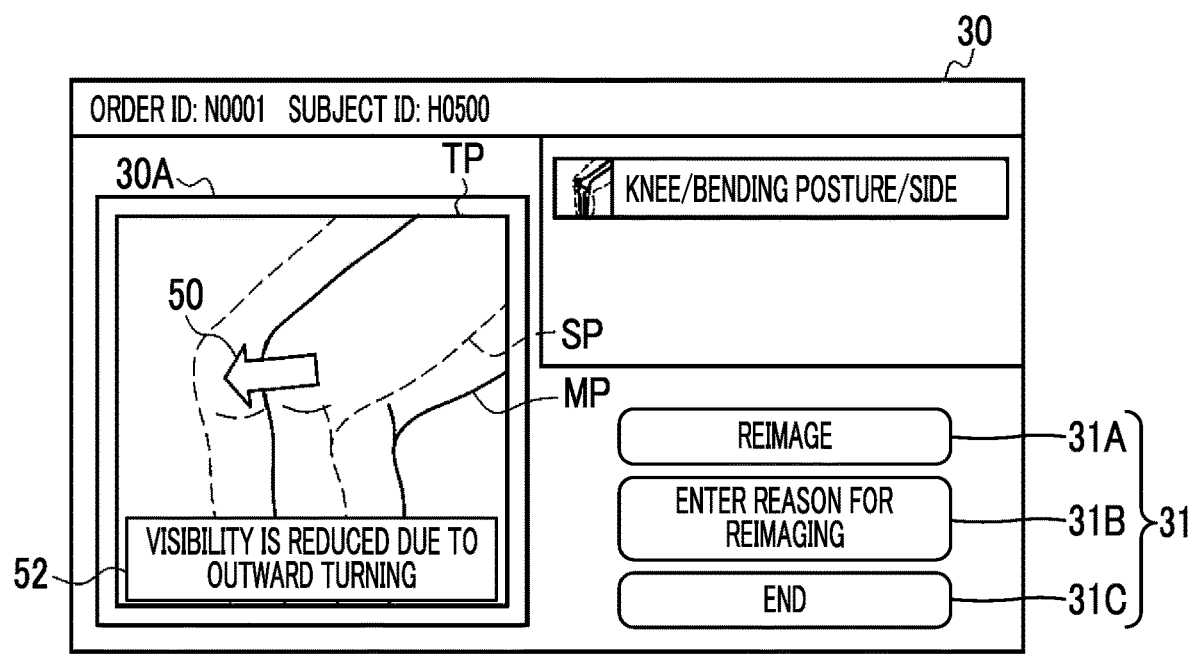
FIG. 17 is a diagram exemplifying an example of a screen of the display on which a superimposition image is displayed.

FIG. 17 shows an example of a screen of the display 30 on which the superimposition image TP is displayed. As shown in FIG. 17, the superimposition image TP is displayed on the display 30 in the image display region 30A. The arrow 50 and the reason for imaging failure 52 are combined and displayed on the superimposition image TP. The technician RG can check whether or not the position of the subject H has moved from the time of the imaging failure on the basis of the superimposition image TP. In a case where the subject H has moved, the technician RG gives an instruction to the subject H with voice or the like on the basis of the arrow 50 or the like, and thus temporarily determines the current position of the subject H (the position indicated by the motion picture MP) to the position at the time of imaging failure (the position indicated by the still image SP).

After temporarily determining the position of the subject H to the position at the time of imaging failure, the technician RG can finely adjust the position of the subject H such that the imaging failure does not occur at the time of reimaging by referring to the reason for imaging failure 52. The X-ray image XP may be displayed on the display 30 in addition to the superimposition image TP. The technician RG can finely adjust the position of the subject H by referring to the X-ray image XP in addition to the reason for imaging failure 52. After that, in a case where the fine adjustment of the position of the subject H is completed, the technician RG presses the irradiation switch 16 to execute the reimaging.

Referring to FIG. 12 again, in a case where the technician RG presses the irradiation switch 16 and thus the still image capturing instruction unit 41 receives the X-ray irradiation start signal ES (step S24: YES), the still image capturing instruction unit 41 instructs the optical camera 15 to execute still image capturing (step S11). In a case where an instruction for executing still image capturing is received, the optical camera 15 finishes motion picture capturing and performs still image capturing. Thereafter, the same process is executed.

Hereinafter, the effect of the imaging support device having the above configuration will be described with reference to FIGS. 18 and 19. In a case of performing X-ray imaging, depending on imaging sites, even though the technician RG thinks that the subject H is positioned accurately, the actual positioning is not performed properly, and as a result, imaging failure may occur. For example, in a case of diagnosing a joint of the knee, the joint cavity JC needs to be clearly depicted in the X-ray image XP, but since X-rays are a flux of light that radially diverges from the focal point of the X-ray source 11, an incidence angle of X-rays changes due to a slight misregistration of the joint, and the depiction of the joint cavity JC becomes unclear. In a case where the depiction of the joint cavity JC is unclear, there is imaging failure and reimaging is required.

In a case where reimaging is required due to imaging failure as described above, the technician RG needs to position the subject H again. In a case of adjusting a slight misregistration of the subject H in order to perform reimaging, it is often sufficient to perform fine adjustment on the basis of a position of the subject H at the time of imaging failure.

Figure 18:
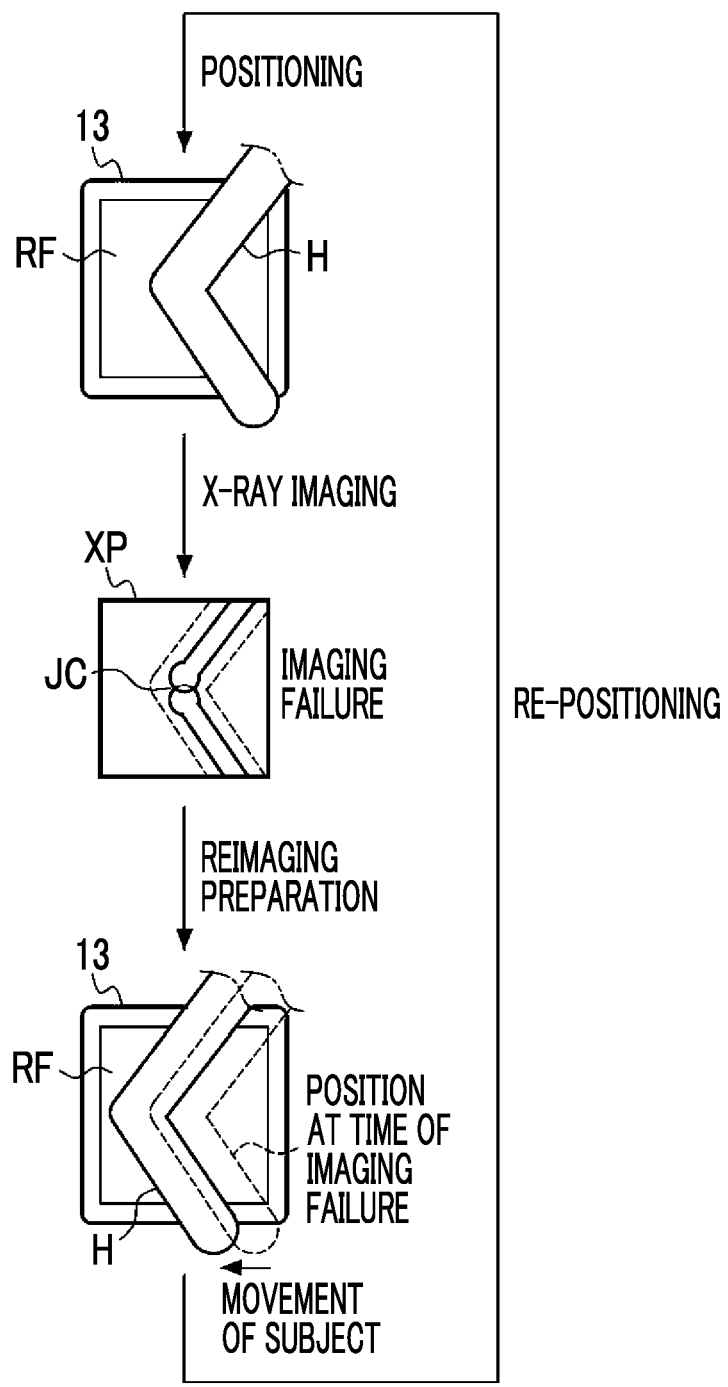
FIG. 18 is a diagram exemplifying a problem in the related art.

However, as shown in FIG. 18, in the technique of the related art, in a case where the subject H moves significantly from the time of imaging failure, the technician RG cannot accurately ascertain the position of the subject H at the time of imaging failure, and thus cannot perform fine adjustment. In a case where the technician RG repositions the subject H from the beginning, there is a high possibility that the subject H will be positioned to the same position again, and the imaging failure will occur again. As described above, in the technique of the related art, even though the subject H is positioned by using an optical camera or the like before X-ray imaging, in a case where the imaging failure occurs, since the technician RG cannot ascertain the position of the subject H at the time of imaging failure, there is a high possibility that imaging failure will occur again, and reimaging will be repeated.

Figure 19:
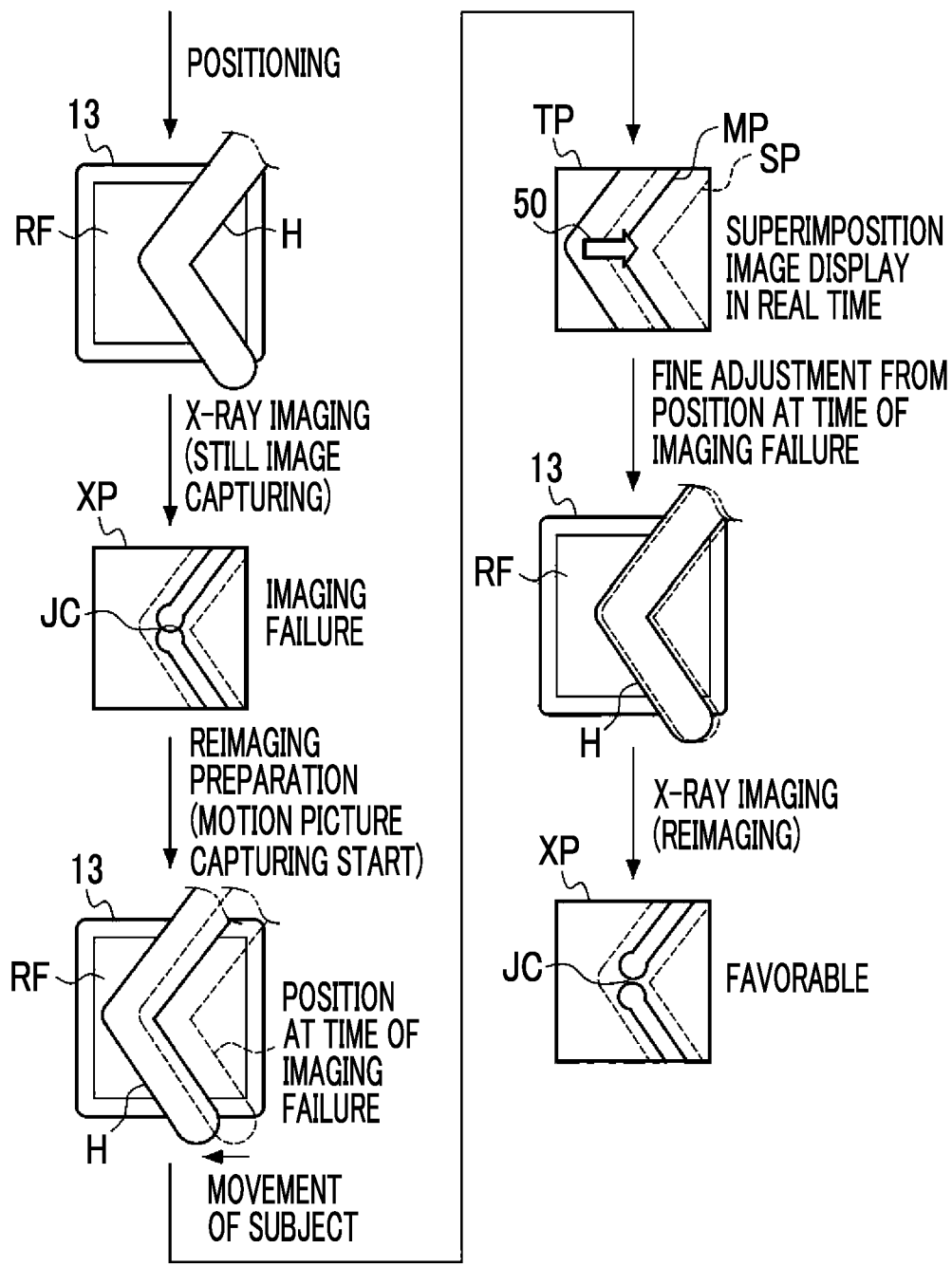
FIG. 19 is a diagram exemplifying the effect of the technique of the present disclosure.

In contrast, as shown in FIG. 19, in the technique of the present disclosure, since an optical image (still image SP) indicating the subject H is acquired in conjunction with X-ray imaging, even though the subject H moves significantly from the time of imaging failure, the technician RG can easily ascertain the position of the subject H at the time of imaging failure. Therefore, the technician RG can position the subject H to the position at the time of imaging failure and then finely adjust the position of the subject H from the position at the time of imaging failure on the basis of a reason for the imaging failure or the like. The favorable X-ray image XP can be obtained by finely adjusting the position of the subject H and then performing reimaging. As described above, according to the technique of the present disclosure, it is possible to suppress the repetition of reimaging. As a result, unnecessary exposure to the subject H can be suppressed and the examination time can be reduced.

In the technique of the present disclosure, the superimposition image TP in which the optical image (still image SP) acquired in conjunction with the X-ray imaging and the current optical image (motion picture MP) of the subject H are superimposed is displayed in real time. Even though the subject H moves significantly from the time of the imaging failure, the technician RG can more easily ascertain the position of the subject H at the time of imaging failure on the basis of the still image SP in the superimposition image TP.

Modification Example of First Embodiment

Next, various modification examples of the first embodiment will be described. In the first embodiment, the display 30 that provides a notification of notification information generated by the notification information generation unit 49 is used as a notification device, and a direction in which the current position of the subject H is moved to the position of the subject H at the time of imaging failure is indicated by an arrow. This notification information may be text or may be an arrow added with text. The notification information may be reported with voice by using a speaker as a notification device.

Figure 20:
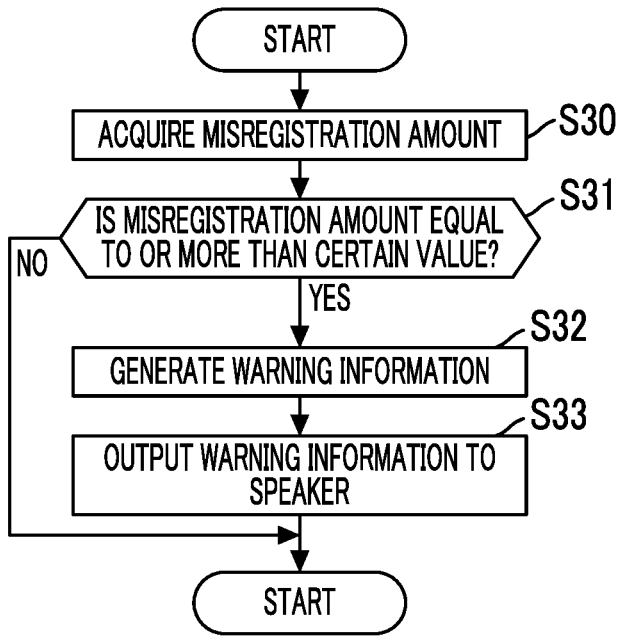
FIG. 20 is a flowchart exemplifying a warning generation process based on a misregistration amount.

The notification information generation unit 49 may generate warning information for giving a warning to the technician RG in a case where a misregistration amount detected by the misregistration detection unit 48 is equal to or more than a certain value. For example, the notification information generation unit 49 performs a process shown in FIG. 20 in parallel to the notification information generation process (step S22) described in the above embodiment. As shown in FIG. 20, the notification information generation unit 49 acquires a misregistration amount (for example, a magnitude of a vector representing a direction) from the misregistration detection unit 48 (step S30), and determines whether or not the acquired misregistration amount is equal to or more than a certain value (step S31). In a case where the misregistration amount is equal to or more than the certain value (step S31: YES), the notification information generation unit 49 generates warning information (step S32), and outputs the generated warning information from a speaker as a notification device (step S33).

A warning sound or a voice indicating that the misregistration amount is equal to or more than the certain value is output from the speaker to the technician RG. Consequently, the technician RG can recognize that the subject H has moved even in a case where the technician RG is not looking at the screen of the display 30. The notification device for reporting the warning information is not limited to a speaker, and may be any one that stimulates perception (auditory, visual, or the like) of the technician RG. The display 30 may be used as a notification device, and a message indicating a warning may be displayed on a screen thereof.

In the first embodiment, as shown in FIG. 14, the reason for imaging failure can be entered by the technician RG using the keyboard 31K or the like, but the CPU 32 may be configured to automatically determine the reason for imaging failure from the X-ray image XP through a machine learning method using a neural network. The neural network learns data in which the X-ray image XP in which imaging failure has occurred is associated with the reason for the imaging failure as training data, and can thus determine reasons for imaging failure such as outward turning, inward turning, and angles thereof for the new X-ray image XP in which the imaging failure has occurred.

In the first embodiment, as shown in FIG. 17, a position of the subject H is moved to the position at the time of imaging failure by the technician RG on the basis of the arrow 50 displayed on the superimposition image TP. Alternatively, a relative position of the subject H with respect to the irradiation field RF may be moved to the position at the time of imaging failure by moving the irradiation field RF of X-rays without changing the position of the subject H.

Figure 21:
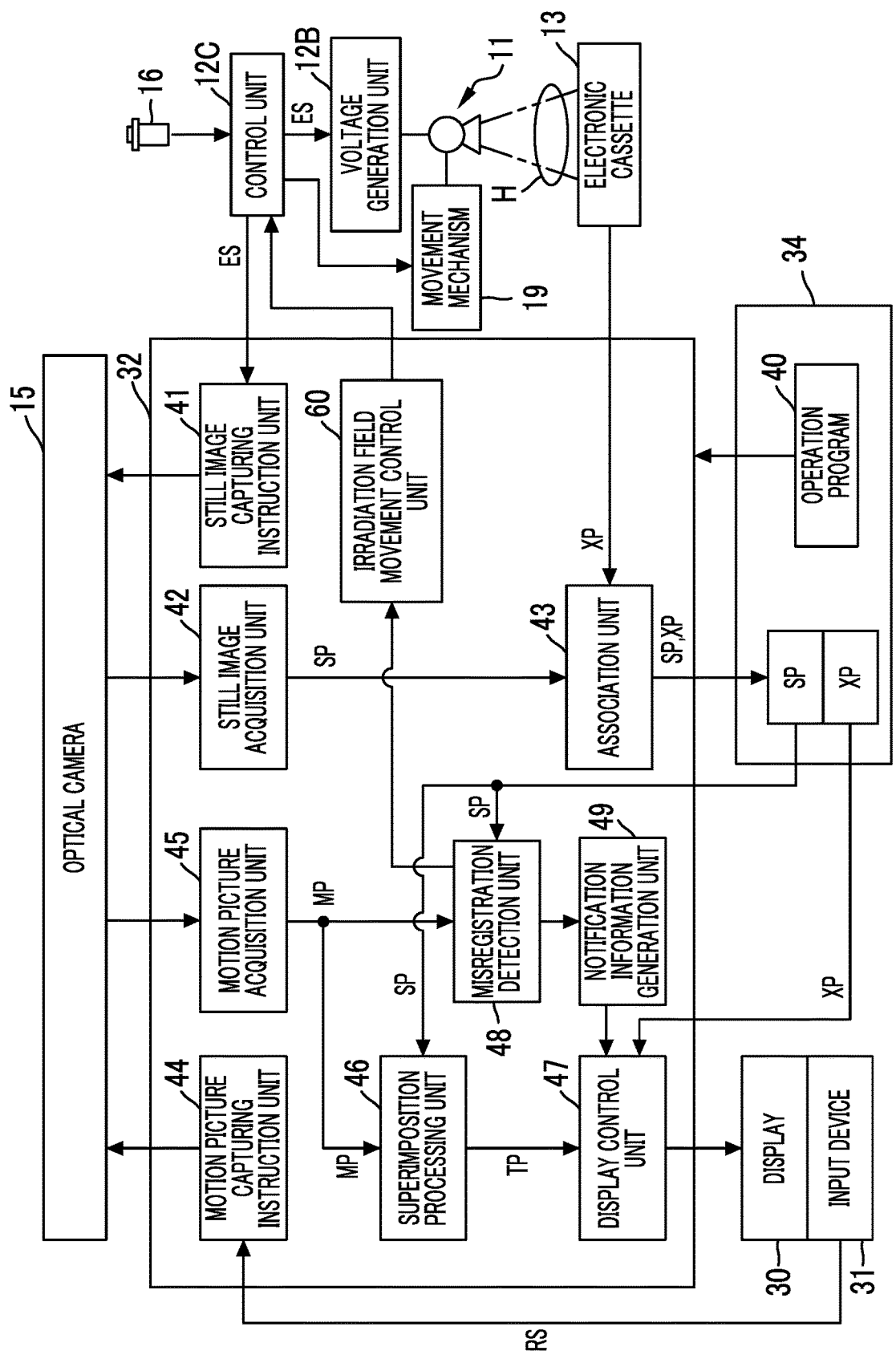
FIG. 21 is a block diagram showing each functional unit of a CPU according to a modification example.
Figure 22:
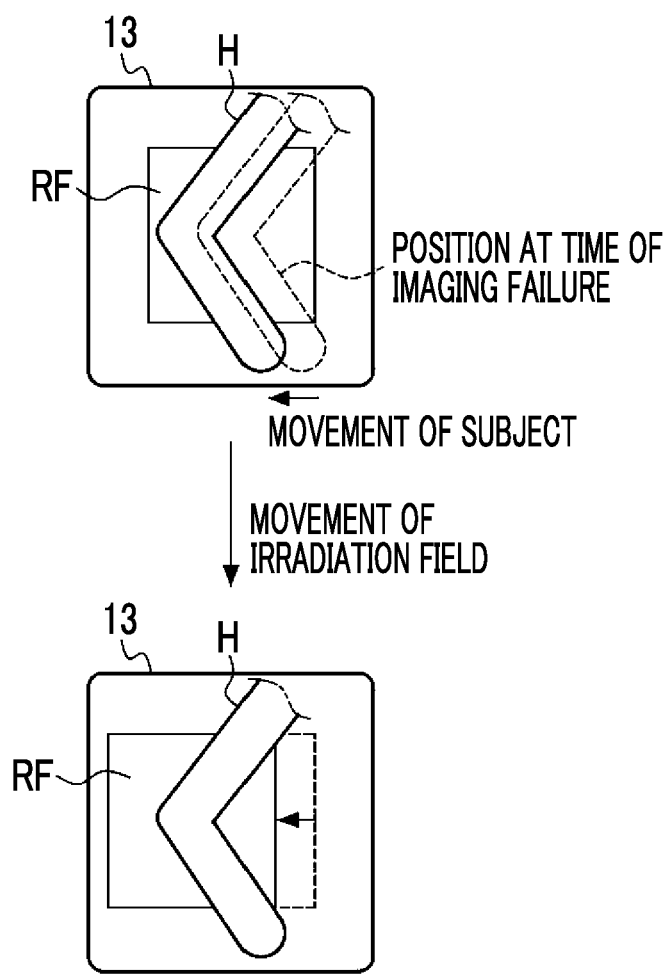
FIG. 22 is a diagram exemplifying movement control of an irradiation field.

In the present modification example, as shown in FIG. 21, an irradiation field movement control unit 60 that controls movement of the irradiation field RF is added to the CPU 32 of the console 14. The irradiation field movement control unit 60 controls a movement mechanism 19 that moves the X-ray source 11 via the control unit 12C of the radiation source control device 12 on the basis of a misregistration amount detected by the misregistration detection unit 48. The movement mechanism 19 is configured with the above suspension holding mechanism 17 and the horizontal movement mechanism 18. As shown in FIG. 22, the irradiation field movement control unit 60 moves the irradiation field RF in a direction in which a misregistration amount detected by the misregistration detection unit 48 decreases, and thus a relative position of the subject H with respect to the irradiation field RF is moved to the position at the time of imaging failure.

In an example shown in FIG. 22, the electronic cassette 13 is fixed, but in a case where the electronic cassette 13 is configured to be movable in conjunction with movement of the X-ray source 11, the electronic cassette 13 may be moved in correlation with movement of the irradiation field RF.

Second Embodiment

Figure 23:
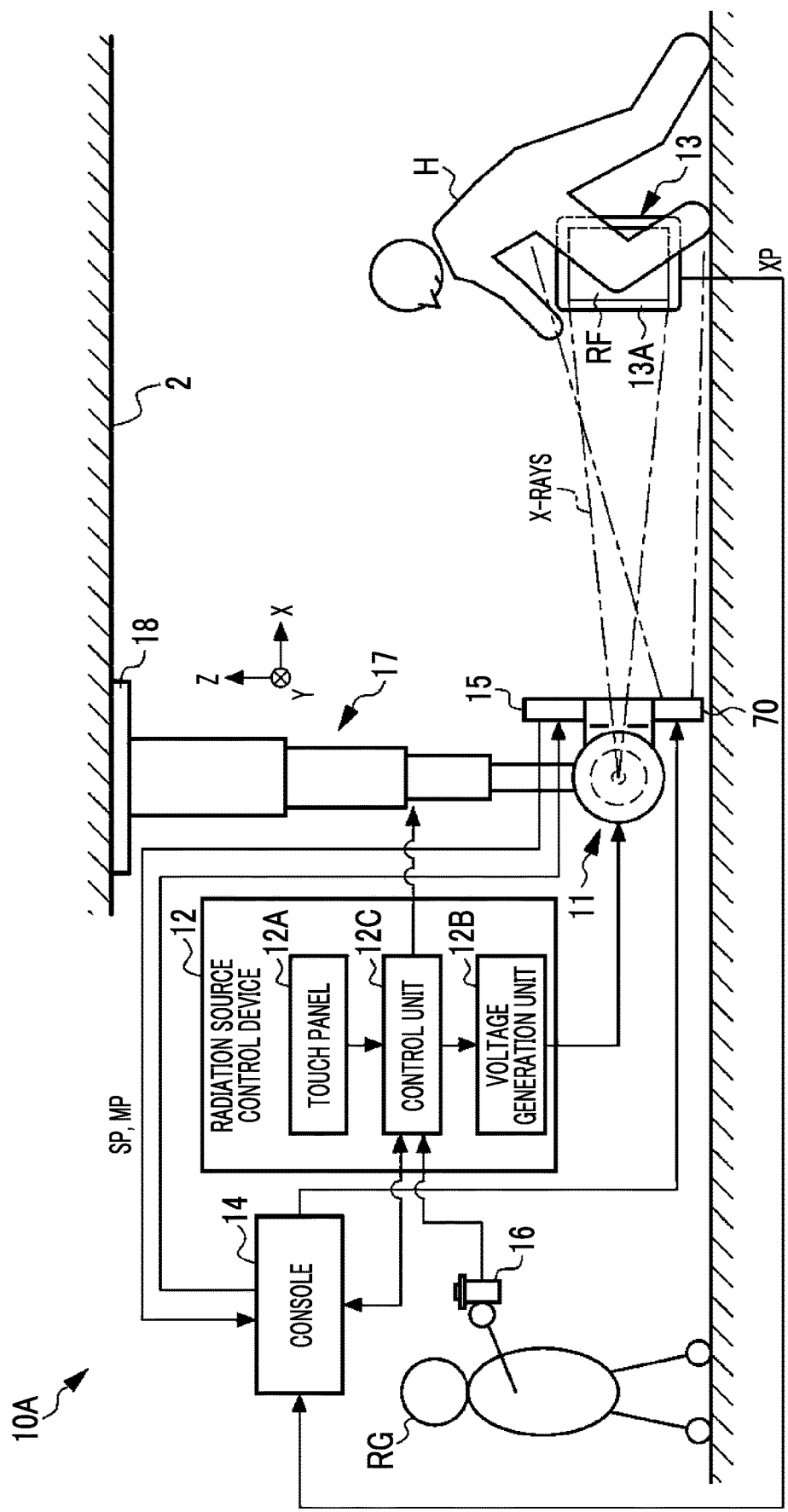
FIG. 23 is a diagram showing a configuration of an X-ray imaging system according to a second embodiment.

Next, a second embodiment of the present disclosure will be described. In FIG. 23, an X-ray imaging system 10A according to the second embodiment includes a projector 70 in addition to the configuration of the X-ray imaging system 10 according to the first embodiment. In the present embodiment, an imaging support device is configured by the CPU 32, the optical camera 15, and the projector 70.

The projector 70 is attached to the outer peripheral portion of the X-ray source 11. The projector 70 is, for example, a small laser projector, and is disposed to project a projection image toward the X-ray incident surface 13A of the electronic cassette 13.

Figure 24:
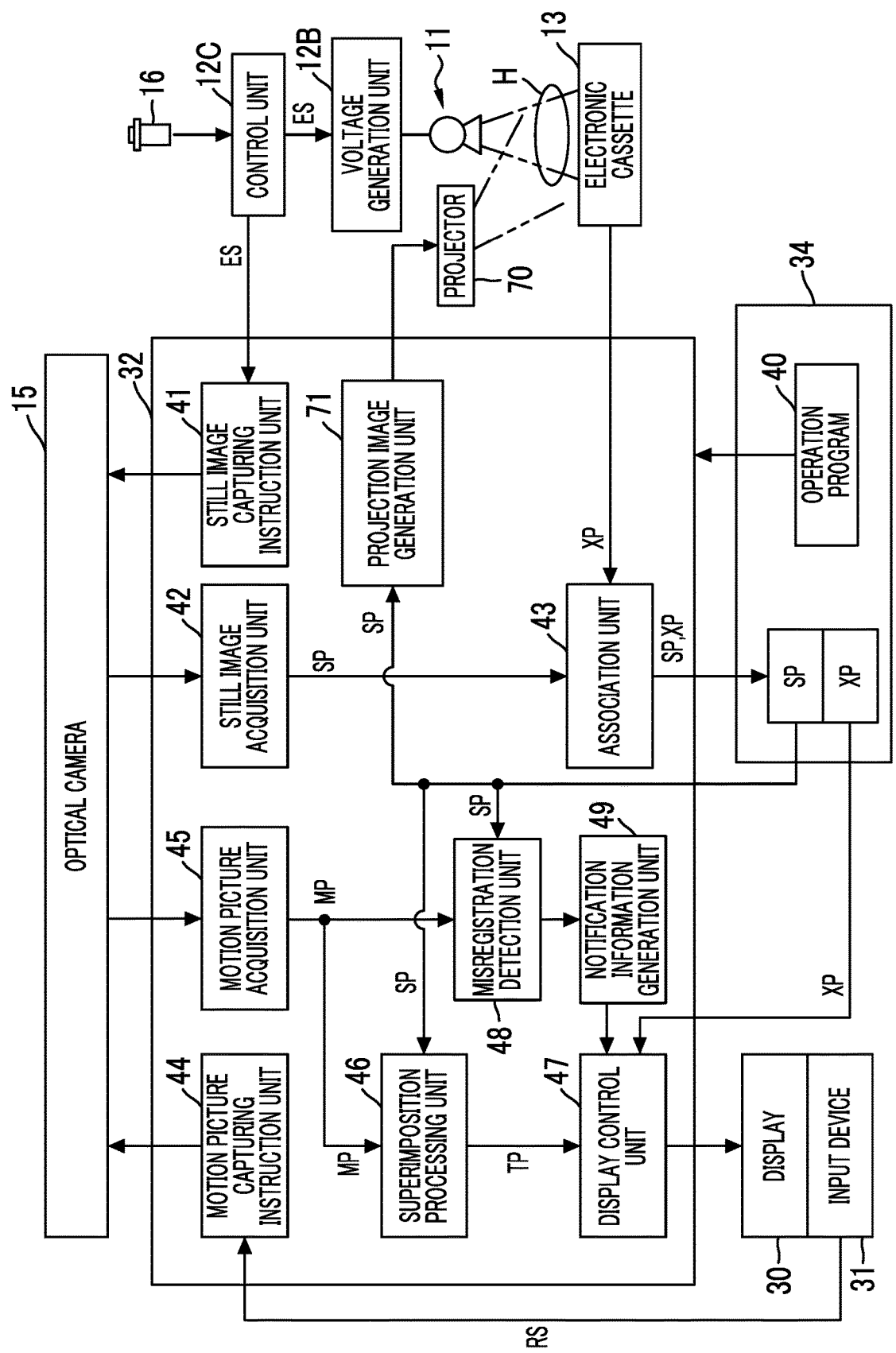
FIG. 24 is a block diagram showing each functional unit of a CPU according to the second embodiment.

In the present embodiment, as shown in FIG. 24, a projection image generation unit 71 that generates a projection image to be supplied to the projector 70 is added to the CPU 32 of the console 14. The projection image generation unit 71 acquires the still image SP captured by the optical camera 15 and stored in the storage device 34 in association with the X-ray image XP by the association unit 43, and generates a projection image.

The projection image generation unit 71 supplies the generated projection image to the projector 70, and causes the projector 70 to project the projection image toward the electronic cassette 13. The projection image generation unit 71 performs projection in a state in which the subject H is located between the X-ray source 11 and the electronic cassette 13 during a reimaging preparation period in which the superimposition image TP is displayed on the display 30. Other configurations of the X-ray imaging system 10A are the same as the configurations of the X-ray imaging system 10 according to the first embodiment.

Figure 25:
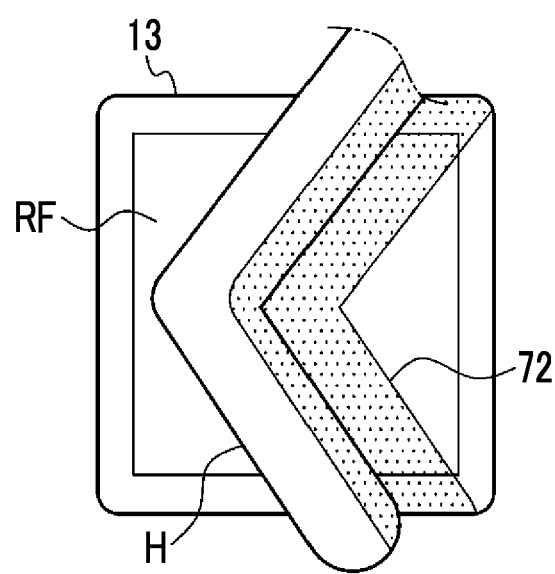
FIG. 25 is a diagram exemplifying a projection image projected onto an electronic cassette.

FIG. 25 exemplifies a projection image 72 projected onto the electronic cassette 13 by the projector 70. In FIG. 25, the projection image 72 is an image indicating the subject H at the time of imaging failure, and a part of the projection image 72 is projected on the surface of the subject H. In the present embodiment, the technician RG can move a position of the subject H to the position at the time of imaging failure by adjusting the position of the subject H such that the subject H overlaps the projection image 72 in a case of preparing for reimaging.

Third Embodiment

Figure 26:
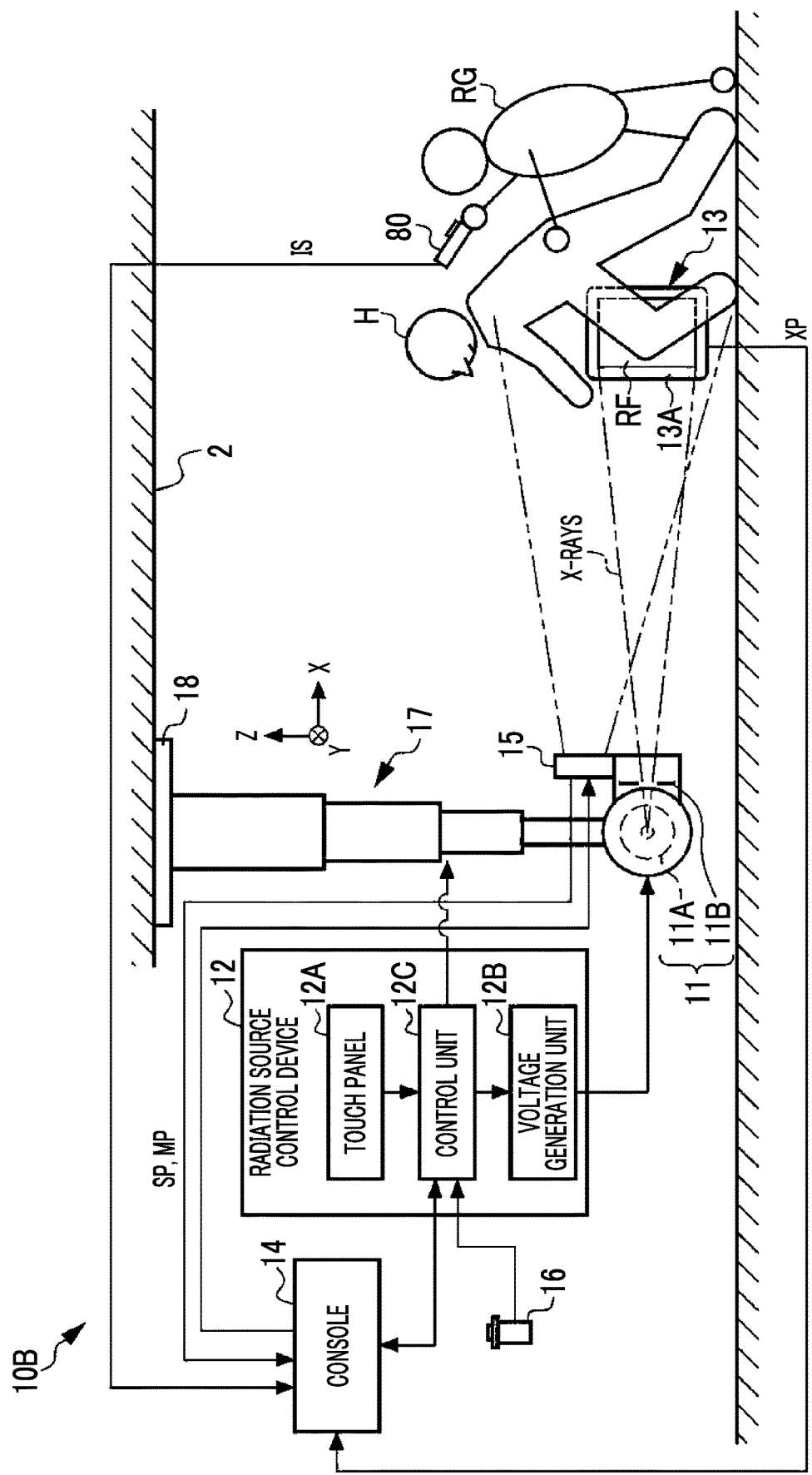
FIG. 26 is a diagram showing a configuration of an X-ray imaging system according to a third embodiment.
Figure 27:
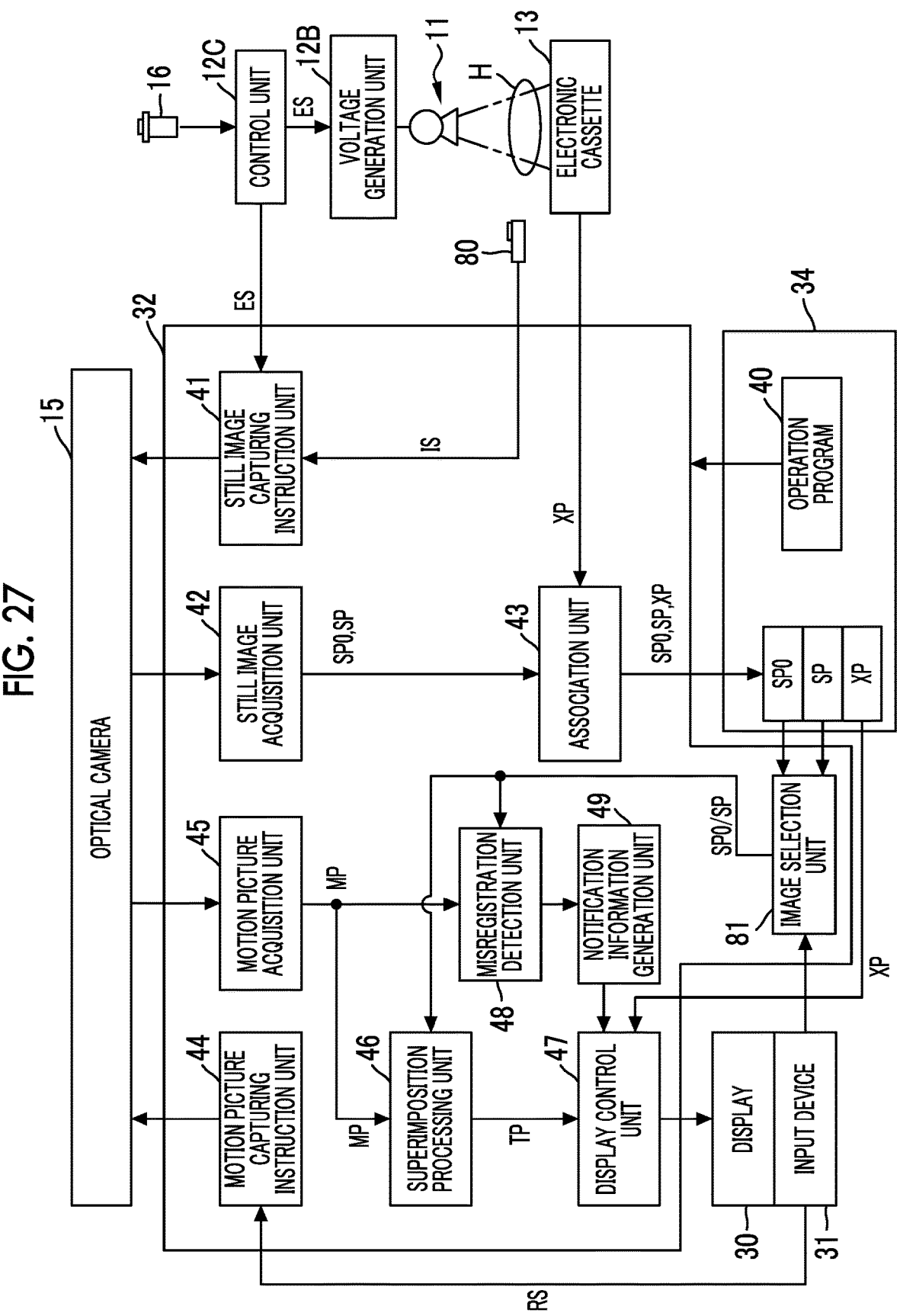
FIG. 27 is a block diagram showing each functional unit of a CPU according to the third embodiment.

Next, a third embodiment of the present disclosure will be described. In FIG. 26, an X-ray imaging system 10B according to the third embodiment includes a remote controller 80 that causes the optical camera 15 to capture a still image in addition to the configuration of the X-ray imaging system 10 according to the first embodiment. In the present embodiment, an imaging support device is configured by the CPU 32, the optical camera 15, and the remote controller 80.

The remote controller 80 is connected to the console 14 by wire or wirelessly. By operating the remote controller 80, the technician RG can transmit an imaging command signal IS from the imaging room to the console 14. The technician RG gives an instruction for still image capturing by operating the remote controller 80 in a case where the subject H has been positioned before performing X-ray imaging.

The console 14 receives the imaging command signal IS from the remote controller 80 via the communication unit 35. The optical camera 15 may be provided with a receiving unit for the imaging command signal IS transmitted from the remote controller 80.

In the present embodiment, the still image capturing instruction unit 41 receives the imaging command signal IS transmitted from the remote controller 80 in addition to the X-ray irradiation start signal ES transmitted from the control unit 12C. Upon receiving the imaging command signal IS, the still image capturing instruction unit 41 instructs the optical camera 15 to execute still image capturing. The still image acquisition unit 42 acquires a still image SP0 captured on the basis of the instruction from the remote controller 80 in addition to the still image SP captured by the optical camera 15 in conjunction with the X-ray imaging. The association unit 43 stores the still image SP0 acquired at the time of positioning the subject H in the storage device 34 in association with the X-ray image XP and the still image SP acquired at the time of subsequent X-ray imaging.

In the present embodiment, an image selection unit 81 is added to the CPU 32. The image selection unit 81 selects an image to be supplied to the superimposition processing unit 46 and the misregistration detection unit 48 on the basis of an operation signal input from the input device 31. Specifically, the image selection unit 81 selects which of the still image SP0 and the still image SP stored in the storage device 34 in association with each other is supplied to the superimposition processing unit 46 and the misregistration detection unit 48 on the basis of the operation signal.

The superimposition processing unit 46 acquires the image (the still image SP0 or the still image SP) selected by the image selection unit 81, superimposes the acquired image on each frame of the motion picture MP, and generates the superimposition image TP. The misregistration detection unit 48 acquires the image (the still image SP0 or the still image SP) selected by the image selection unit 81, and detects a misregistration amount of the subject H between the acquired image and each frame of the motion picture MP. Other configurations of the X-ray imaging system 10B are the same as the configurations of the X-ray imaging system 10 according to the first embodiment.

Next, an operation of the imaging support device according to the third embodiment will be described with reference to the flowcharts of FIGS. 28 and 29. Prior to X-ray imaging, the technician RG positions the subject H with respect to the X-ray source 11 and the electronic cassette 13 (refer to FIG. 26). The technician RG instructs the optical camera 15 to execute still image capturing by operating the remote controller 80 in a state in which the subject H is positioned to a desired position.

The still image capturing instruction unit 41 determines whether or not the imaging command signal IS has been received from the remote controller 80 (step S40). In a case where the imaging command signal IS has been received (step S40: YES), the still image capturing instruction unit 41 instructs the optical camera 15 to execute still image capturing (step S41). The still image acquisition unit 42 acquires the still image SP0 generated by the optical camera 15 capturing a still image (step S12). The still image SP0 acquired by the still image acquisition unit 42 is stored in the storage device 34 via the association unit 43 (step S43).

Thereafter, the technician RG operates the input device 31 to start preparing for X-ray imaging. In a case where it is determined whether or not an imaging preparation start signal has been received from the input device 31 (step S44) and the imaging preparation start signal has been received (step S44: YES), the motion picture capturing instruction unit 44 transmits a motion picture capturing start signal to the optical camera 15 (step S45). The motion picture acquisition unit 45 acquires the motion picture MP generated by the optical camera 15 capturing a motion picture for each frame (step S46).

The superimposition processing unit 46 acquires an image stored in the storage device 34. Here, the still image SP0 is selected by the image selection unit 81. The superimposition processing unit 46 acquires the still image SP0 via the image selection unit 81, performs a process of superimposing the still image SP0 on the frame of the motion picture MP acquired by the motion picture acquisition unit 45, and generates the superposition image TP (step S47).

The misregistration detection unit 48 acquires the still image SP0 stored in the storage device 34 via the image selection unit 81, and detects a misregistration amount of the subject H between the frame of the motion picture MP acquired by the motion picture acquisition unit 45 and the still image SP0 (step S48). The notification information generation unit 49 generates notification information indicating a direction (vector) in which the current position of the subject H is moved to the position of the subject H at the time of initial positioning on the basis of the misregistration amount detected by the misregistration detection unit 48 (step S49).

The display control unit 47 generates an arrow indicating the direction included in the notification information, and displays the arrow on the display 30 in a state in which the arrow is combined on the superimposition image TP (step S50). Thereafter, similarly to step S10 shown in FIG. 12 in the first embodiment, it is determined whether or not the still image capturing instruction unit 41 has received the X-ray irradiation start signal ES from the control unit 12C (step S51).

While the still image capturing instruction unit 41 does not receive the X-ray irradiation start signal ES (step S51: NO), the process returns to step S46, and the motion picture acquisition unit 45 acquires the next frame of the motion picture MP. Until the X-ray irradiation start signal ES is received, the processes in steps S46 to S51 are repeatedly executed. Consequently, the superimposition image TP in which the still image SP0 is superimposed on the motion picture MP is displayed on the display 30 in real time.

The superimposition image TP displayed on the display 30 is the same as the superimposition image TP shown in FIG. 17 in the first embodiment. The technician RG can check whether or not the position of the subject H has been moved from the time of initial positioning on the basis of the superimposition image TP. In a case where the subject H has moved, the technician RG gives an instruction to the subject H with voice or the like on the basis of an arrow or the like displayed on the superimposition image TP, and thus the current position of the subject H (indicated by the motion picture MP) is moved to the position at the time of positioning (the position indicated by the still image SP0).

In a case where the technician RG presses the irradiation switch 16 and thus the still image capturing instruction unit 41 receives the X-ray irradiation start signal ES (step S51: YES), the still image capturing instruction unit 41 instructs the optical camera 15 to execute still image capturing (step S52). Since the processes in steps S52 to S65 are the same as the processes in steps S11 to S24 shown in FIG. 12 in the first embodiment, the description thereof will be omitted. In the present embodiment, the X-ray image XP and the still image SP captured in conjunction with the X-ray imaging are stored in the storage device 34 in association with the still image SP0.

Figure 30:
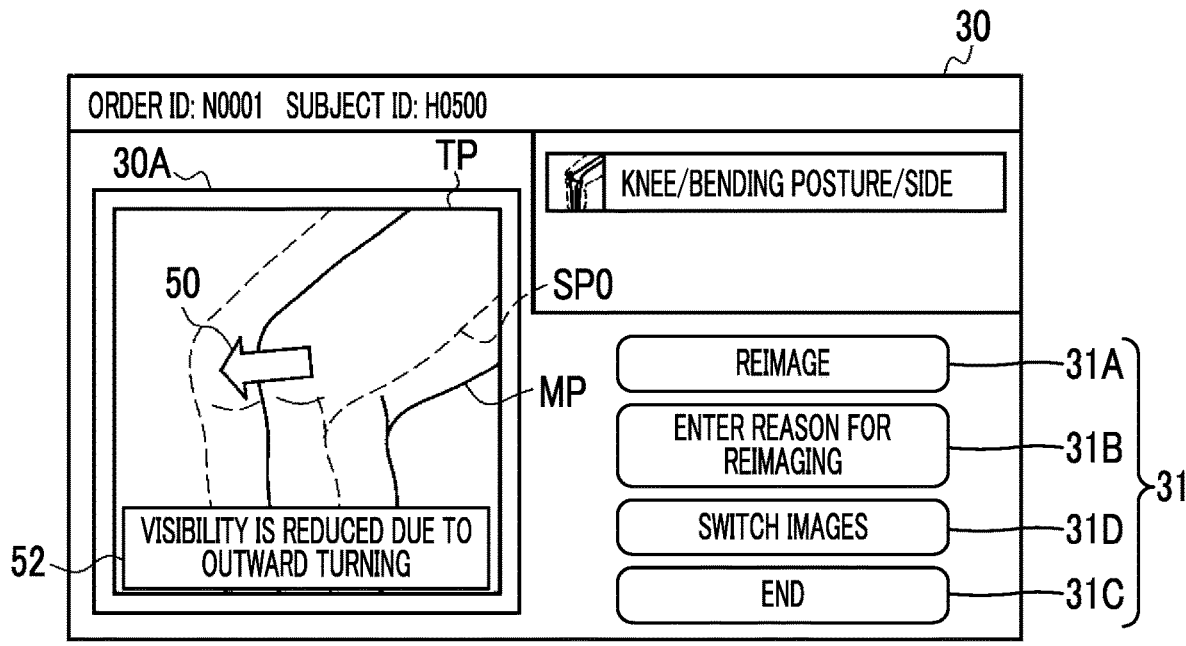
FIG. 30 is a diagram exemplifying a screen at the time of preparation for reimaging in the third embodiment.

In the present embodiment, it is possible to select an image (the still image SP0 or the still image SP) to be superimposed on the motion picture MP when preparing for reimaging. For example, as shown in FIG. 30, on the screen of the display 30, in addition to the first to third operation buttons 31A to 31C, a fourth operation button 31D for switching between images is displayed. By operating the fourth operation button 31D, the technician RG can switch an image to be superimposed on the motion picture MP between the still image SP0 acquired at the time of initial positioning and the still image SP acquired at the time of imaging failure. Consequently, the technician RG can also move the position of the subject H to the position of the subject H at the time of initial positioning and perform reimaging.

Figure 31:
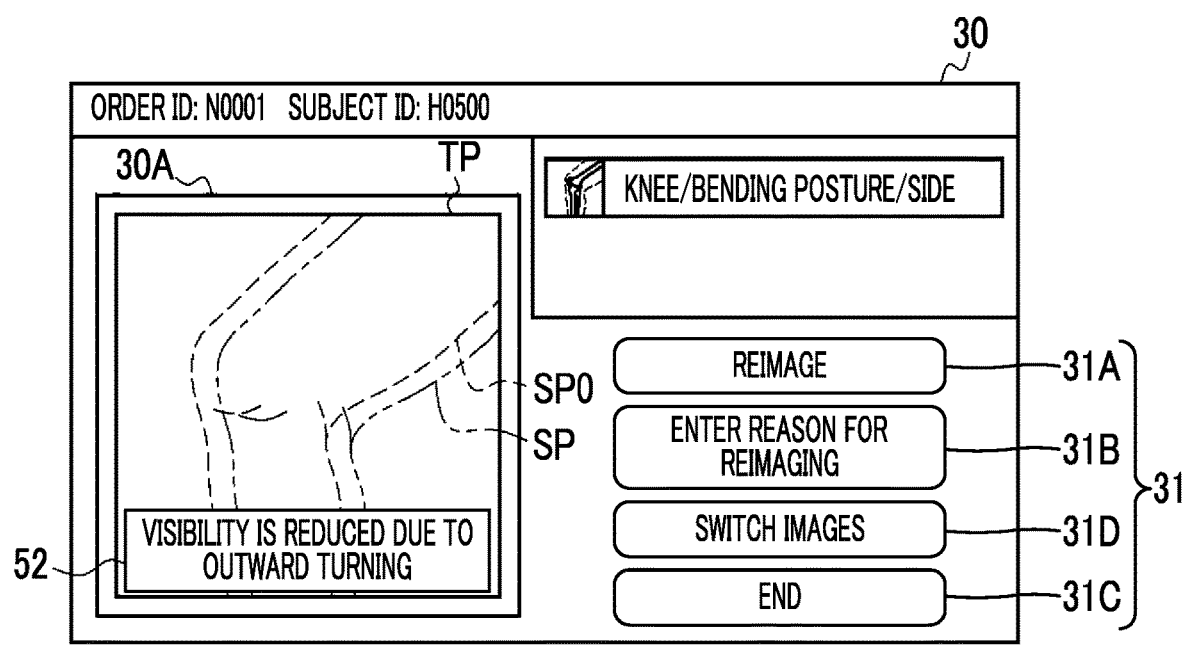
FIG. 31 is a diagram showing another display example of a screen at the time of preparation for reimaging in the third embodiment.

As shown in FIG. 31, it is also preferable to enable superimposition display of the still image SP0 acquired at the time of initial positioning and the still image SP acquired at the time of imaging failure. Consequently, the technician RG can determine whether imaging failure has occurred due to movement of the subject H from initial positioning or the imaging failure has occurred despite the subject H not having moved since initial positioning.

Figure 12:
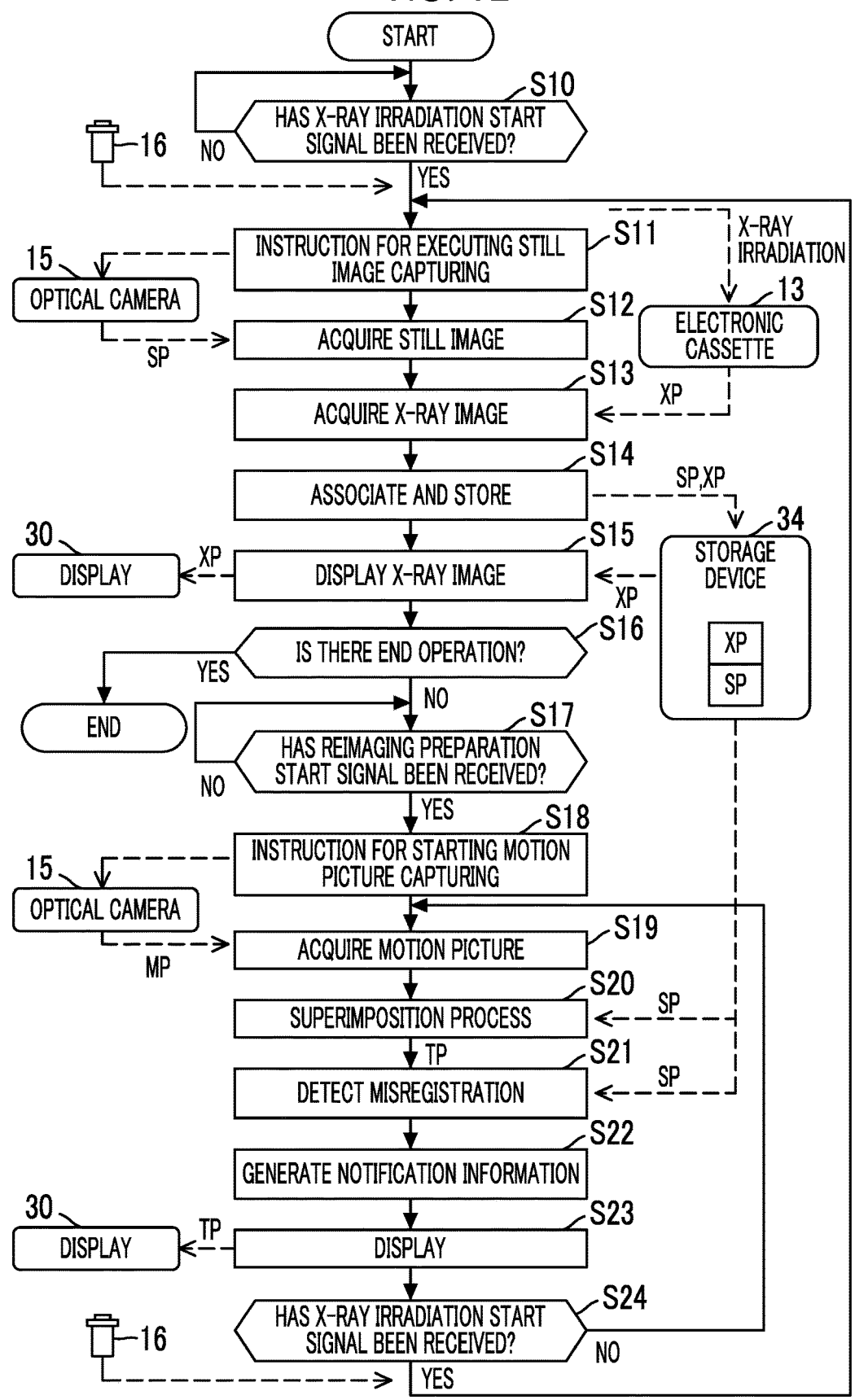
FIG. 12 is a flowchart for describing a process procedure of the CPU.
Figure 28:
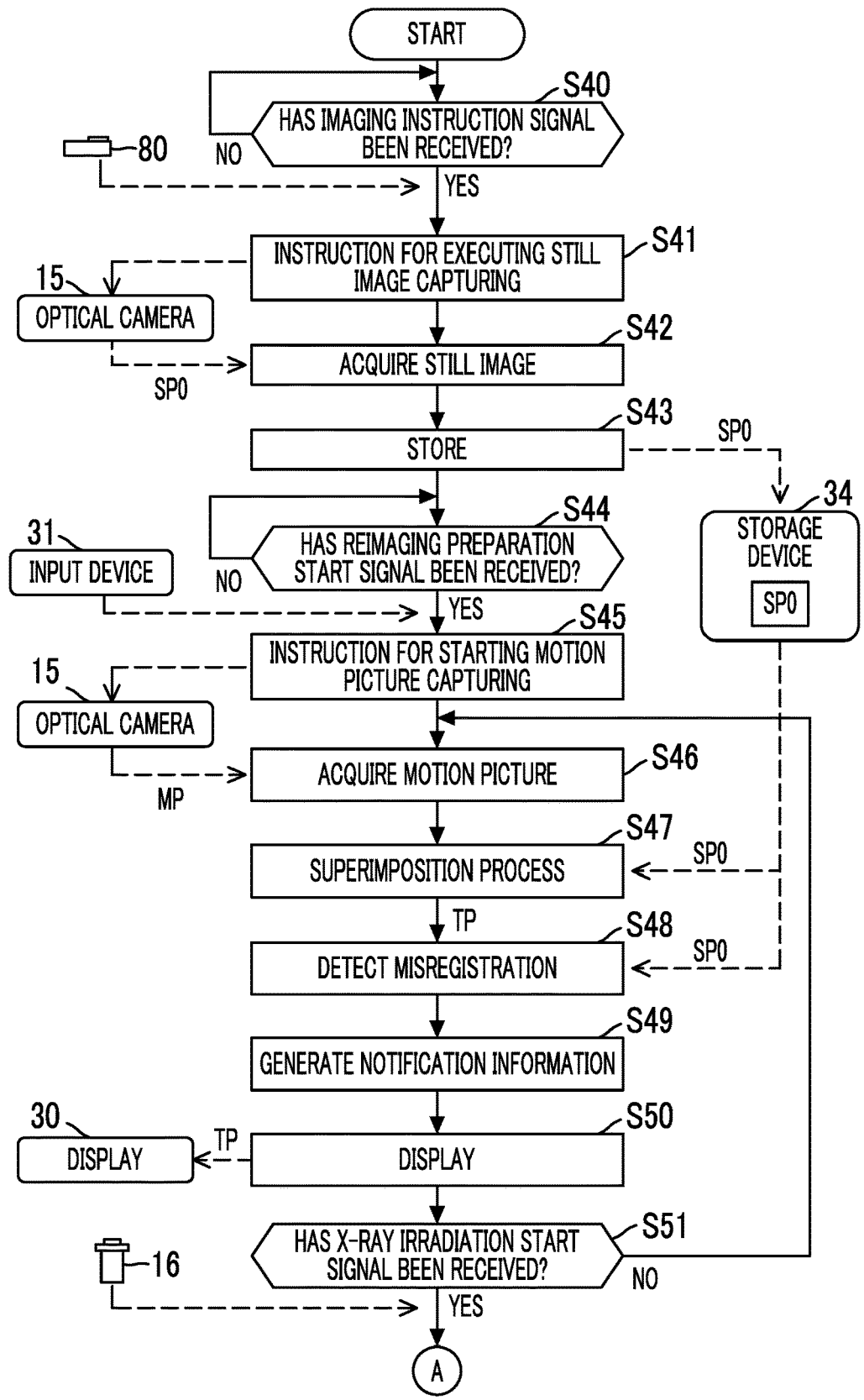
FIG. 28 is a flowchart (first) for describing a process procedure of the CPU according to the third embodiment.
Figure 29:
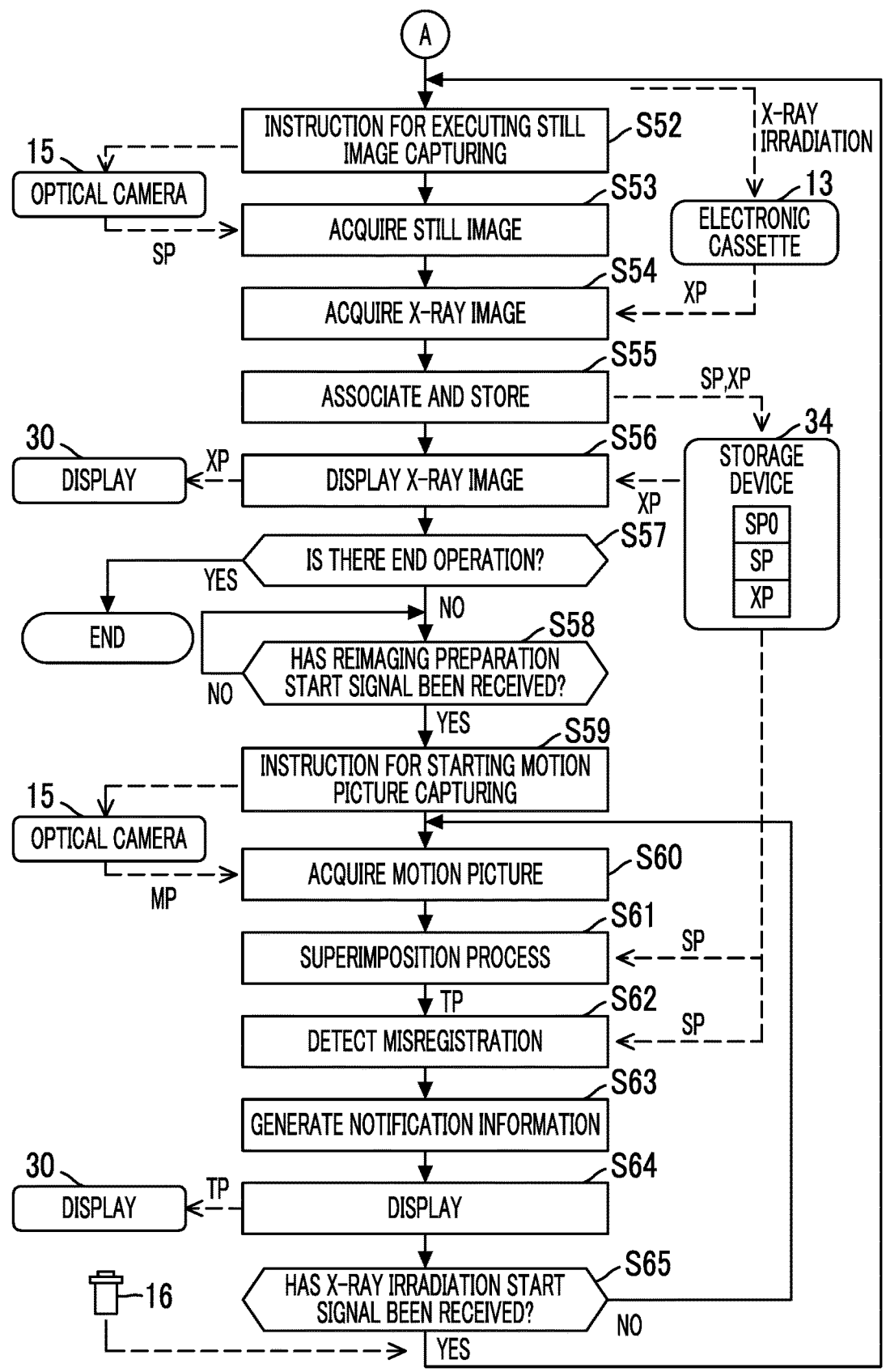
FIG. 29 is a flowchart (second) for describing the process procedure of the CPU according to the third embodiment.

The order of the processes included in the flowchart of FIG. 12 in the first embodiment and the flowcharts of FIGS. 28 and 29 in the third embodiment may be appropriately changed as long as there is no contradiction. Needless to say, acquisition of a still image, acquisition of an X-ray image, a superposition process, detection of misregistration, and the like may be performed in a temporally overlapping manner.

The optical camera 15 may be attached to a location other than the X-ray source 11, such as a wall or a ceiling of the imaging room, as long as the subject H located in the irradiation field RF can be imaged. The optical camera 15 is not limited to visible light, and may be any camera that optically performs imaging. For example, the optical camera 15 may be an infrared camera that performs imaging on the basis of infrared rays.

The projector 70 may be attached to a location other than the X-ray source 11, such as a wall or a ceiling of the imaging room, as long as an image can be projected to the irradiation field RF.

Each of the above embodiments has been described by exemplifying the X-ray imaging system provided in the imaging room, but the X-ray imaging system may be one using a so-called mobile visiting car.

The technique of the present disclosure can be applied not only to X-rays but also to a system for imaging a subject by using other radiation such as γ-rays.

In each of the above embodiments, hardware structures of processing units executing various processes, such as the still image capturing instruction unit 41, the still image acquisition unit 42, the association unit 43, the motion picture capturing instruction unit 44, the motion picture acquisition unit 45, the superimposition processing unit 46, the display control unit 47, and the misregistration detection unit 48, the notification information generation unit 49, the irradiation field movement control unit 60, the projection image generation unit 71, and the image selection unit 81 are various processors as described below.

The various processors include a CPU, a programmable logic device (PLD), a dedicated electric circuit, and the like. As is well known, the CPU is a general-purpose processor that executes software (program) and functions as various processing units. The PLD is a processor such as a field programmable gate array (FPGA) of which a circuit configuration can be changed after manufacturing. The dedicated electric circuit is a processor having a circuit configuration specially designed for executing a specific process, such as an application specific integrated circuit (ASIC).

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined.

It goes without saying that the present invention is not limited to each of the above embodiments, and various configurations can be employed without departing from the concept of the present invention. The present invention is applied not only to a program but also to a storage medium storing the program in a non-transitory manner.

What is claimed is:

1. An imaging support device used in a radiography apparatus including a radiation source and a radiation image detector that detects a radiation image of a subject on the basis of radiation emitted from the radiation source and transmitted through the subject, the imaging support device comprising:
    an optical camera that optically images a region including an irradiation field of the radiation applied to the subject from the radiation source; and
    at least one processor, wherein
    the processor
        acquires, as a first optical image, an optical image indicating the subject in the region by causing the optical camera to perform imaging in conjunction with radiography performed by the radiography apparatus,
        stores a radiation image acquired through the radiography and the first optical image in a storage unit in association with each other,
        acquires, as a second optical image, an optical image indicating the subject in the region by causing the optical camera to perform imaging after the radiography is performed, and
        displays a superimposition image, in which the first optical image and the second optical image are superimposed, and the radiation image on the display unit.

2. The imaging support device according to claim 1, wherein the first optical image is a still image, and the second optical image is a motion picture, and
the processor superimposes the second optical image on the first optical image, and displays the superposition result on the display in real time.

3. The imaging support device according to claim 1, wherein the processor
    detects a misregistration amount of the subject between the first optical image and the second optical image through image processing, and
    supplies information regarding the misregistration amount to a notification device.

4. The imaging support device according to claim 3, wherein the notification device is the display, and
the processor displays, on the display, a direction in which a position of the subject is moved to a position indicated by the first optical image on the basis of the misregistration amount.

5. The imaging support device according to claim 3, wherein the processor outputs a warning from the notification device in a case where the misregistration amount is equal to or more than a certain value.

6. The imaging support device according to claim 3, wherein the radiography apparatus further includes a movement mechanism that moves the irradiation field of the radiation, and
the processor controls the movement mechanism such that the irradiation field is moved in a direction in which the misregistration amount decreases.

7. The imaging support device according to claim 1, wherein the optical camera performs imaging on the basis of visible light or infrared rays.

8. The imaging support device according to claim 1, further comprising:
    a projector that projects the first optical image onto the radiation image detector.

9. An operation method for an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source, the operation method comprising:
    acquiring an optical image indicating the subject in the region by causing the optical camera to perform imaging in conjunction with radiography performed by the radiography apparatus;
    storing a radiation image acquired through the radiography and the optical image in a storage device in association with each other;
    acquiring, as a second optical image, an optical image indicating the subject in the region by causing the optical camera to perform imaging after the radiography is performed; and
    displaying a superimposition image, in which the first optical image and the second optical image are superimposed, and the radiation image on the display unit.

10. A non-transitory computer-readable storage medium storing an operation program for operating an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source and at least one processor, the operation program causing the processor to execute:
    an operation of acquiring an optical image indicating the subject in the region by causing the optical camera to perform imaging in conjunction with radiography performed by the radiography apparatus;
    an operation of storing a radiation image acquired through the radiography and the optical image in a storage device in association with each other;
    an operation of acquiring, as a second optical image, an optical image indicating the subject in the region by causing the optical camera to perform imaging after the radiography is performed; and an operation of displaying a superimposition image, in which the first optical image and the second optical image are superimposed, and the radiation image on the display unit.

* * * * *